(12) United States Patent
Ragauskas et al.

(10) Patent No.: US 6,387,051 B1
(45) Date of Patent: May 14, 2002

(54) METHOD AND APPARATUS FOR NON-INVASIVELY DERIVING AND INDICATING OF DYNAMIC CHARACTERISTICS OF THE HUMAN AND ANIMAL INTRACRANIAL MEDIA

(75) Inventors: Arminas Ragauskas; Gediminas Daubaris, both of Kaunas (LT)

(73) Assignee: UAB Vittamed, Bethel, CT (US)

( * ) Notice: Subject to any disclaimer, the term of this patent is extended or adjusted under 35 U.S.C. 154(b) by 0 days.

(21) Appl. No.: 09/663,313

(22) Filed: Sep. 15, 2000

Related U.S. Application Data

(60) Provisional application No. 60/154,080, filed on Sep. 15, 1999.

(51) Int. Cl.⁷ .................................................. A61B 8/00
(52) U.S. Cl. ........................................ 600/438; 600/442
(58) Field of Search ................................. 600/437, 442, 600/438, 443, 447

(56) References Cited

U.S. PATENT DOCUMENTS

| | | |
|---|---|---|
| 3,439,530 A | 4/1969 | Flaherty et al. ............... 73/67.8 |
| 3,713,329 A | 1/1973 | Munger ....................... 73/67.9 |
| 3,818,989 A | 6/1974 | Williams ........................ 128/2 |
| 4,610,255 A | 9/1986 | Shimura et al. ............. 128/660 |
| 5,379,770 A | 1/1995 | Van Veen ............... 128/661.09 |
| 5,388,583 A * | 2/1995 | Ragauskas et al. .......... 600/438 |
| 5,435,312 A * | 7/1995 | Spirey et al. ................ 600/448 |
| 5,514,146 A | 5/1996 | Lam et al. ................... 606/130 |
| 5,785,656 A * | 7/1998 | Chiabrera et al. ........... 600/449 |
| 5,817,018 A | 10/1998 | Ohtomo ....................... 600/437 |
| 5,840,018 A | 11/1998 | Michaeli ..................... 600/300 |
| 5,842,990 A | 12/1998 | Kraske ........................ 600/437 |
| 5,951,476 A | 9/1999 | Beach ......................... 600/437 |
| 5,951,477 A | 9/1999 | Ragauskas et al. .......... 600/437 |

* cited by examiner

*Primary Examiner*—Francis J. Jaworski
(74) *Attorney, Agent, or Firm*—St. Onge Steward Johnston & Reens LLC

(57) ABSTRACT

An ultrasonic method for indicating a characteristic of intraparenchymal brain tissue includes the transmission of broadband ultrasound from a transmitting transducer positioned on one side of a patient's cranium to a receiving transducer located on another side of the cranium with decomposition of the received signal into narrowband components and determination therefrom of group delay, phase angle and attenuation as a basis for derivation of the characteristic of the intraparenchymal tissue within the cranium.

2 Claims, 20 Drawing Sheets

● NEW BLOCKS COMPARING WITH FIG 18
OF OUR PRIOR PATENT NO. 5,388,583

FIG. 8 — ICP PULSE WAVES: (a) - BEFORE THE TEST; (b) - DURING THE TRANSIENT PROCESS; (c) - IN THE HEAD UP POSITION. TIME-OF-FLIGHT PULSE WAVES: (d) - BEFORE THE TEST; (e) - DURING THE TRANSIENT PROCESS; (f) - IN THE HEAD UP POSITION.

METHOD AND APPARATUS FOR NON-INVASIVELY DERIVING AND INDICATING OF DYNAMIC CHARACTERISTICS OF THE HUMAN AND ANIMAL INTRACRANIAL MEDIA

PARENT CASE TEXT

We claim priority benefits under 35 U.S.C. Section 119(e) of U.S. Provisional Patent Application Serial No. 60/154,080 filed Sep. 15, 1999.

U.S. PAT. DOCUMENTS

| | | | |
|---|---|---|---|
| 3872858 | Mar., 1975 | Hudson et al. | 128/2. |
| 4043321 | Aug., 1977 | Soldner et al. | 128/2. |
| 4062354 | Dec., 1977 | Taylor et al. | |
| 4312361 | Jan., 1982 | Nicholson et al. | 600/561. |
| 4690149 | Sep., 1987 | Ko | 128/653. |
| 4819648 | Apr., 1989 | Ko | 128/653. |
| 4971061 | Nov., 1990 | Kageyama et al. | 128/660. |
| 4984567 | Jan., 1991 | Kageyama et al. | 128/660. |
| 5074310 | Dec., 1991 | Mick | 600/561. |
| 5117835 | Jun., 1992 | Mick | 600/561. |
| 5388583 | Feb., 1995 | Ragauskas et al. | 128/661. |
| 5411028 | May., 1995 | Bonnefous | 128/661. |
| 5617873 | Apr., 1997 | Yost et al. | 128/748. |
| 5919144 | Jul., 1999 | Bridger et al. | 600/561. |

OTHER REFERENCES

1. Physical properties of medical ultrasound. Ed. R. Hill. Ellis Horwood Ltd., Publ. 1986, p. 586.
2. Grybauskas P, "Ultrasonic measurements of coagulation", Kaunas, 1998, p. 283 (in Lithuanian).
3. E. Cvetlanova, "Cerebrospinal fluid", Kiev, 1986 (in Russian).
4. Ping He, "Simulation of ultrasound pulse propogation in loosy media obeying a frequency power law", IEEE Transaction on Ultrasonic, Ferroelectrics, and Freqency Control, vol.45, No.1, 114–125, January 1998.
5. Thomas L. Szabo, "Causal theories and data for acoustic attenuation obeying frequency power law." J. Acoust. Soc. Am. 97 (1), 14–24, 1995
6. Margaret G. Wismer, Reinhold Ludwig, "An explicit numerical time domain formulation to simulate pulse pressure waves in viscous fluids exhibiting arbitrary frequency power law attenuation", IEEE Transaction on Ultrasonic, Ferroelectrics, and Freqency Control, Vol.42, No.6, 1040–1049 November 1995.
7. Roman Kuc, "Modeling acoustic attenuation of soft tissue with minimum phase filter", Ultrasonic Imaging 6, 24–36 1984.
8. X. M. Tang, M. N. Toksoz, P. Tarif, R. H. Wilkens, "A method for measuring acoustic wave attenuation in laboratory", J. Acoust. Soc. Am. 93 (2), 453–462, 1988.
9. Ping He, Anthony McGoron, "Parameter estimation for nonlinear frequency dependent attenuation in soft tissue", Ultrasound in Med.& Biol. Vol. 15, No 8, 757–763, 1989.
10. M. O'Donnell, E. T. Jaynes, J. G. Miller "Kramers-Kronig relationship between ultrasonic attenuation and phase velocity", J. Acoust. Soc. Am. 69 (3), 696–701, 1988.
11. W. J. Thoman, S. Lampotang, D. Gravenstein, J. van der Aa, "A computer model of intracranial dynamics", in Proc. IEEE/EMBS 1997 Chicago, Ill. USA, p. 2197.

FIELD OF THE INVENTION

The present invention relates to the measurement and monitoring of intracranial contents' volume and intracranial pressure, and more particularly relates to an apparatus and method for non-invasive measurement of the brain parenchyma blood volume, brain tissue volume and intracranial pressure using ultrasonic pulses.

BACKGROUND OF THE INVENTION

The measurement of intracranial pressure (ICP) is important in diagnosing and treating various pathophysiological conditions caused by head trauma, hemorrhage, tumours, inflammatory diseases and the like. Several techniques have been used to measure ICP. Conventional invasive ICP measurement techniques require surgical passage through the skull bone into the brain ventricles, parenchyma or the region between the skull and dura matter to implant a measuring transducer.

A non-invasive ICP measurement technique has been suggested that determines displacements of the tympanic membrane of the ear. However, it has been not possible to obtain a good correlation with ICP because determination of ICP by this method is complicated by the compressible air space between the pressure source and the interrogation point.

Another non-invasive ICP measurement method measures the electromagnetic impedance response of the brain to induced fields, and correlates the response to ICP. Such techniques are disclosed in U.S. Pat. Nos. 4,690,149 and 4,819,648 to Ko.

Another non-invasive ICP measurement technique that has been attempted involves ultrasonic imaging to detect relative displacements of tissue boundaries within the brain. The displacements may be associated with fluid build-up and compression or dilation of brain vessels, which permits determination of ICP through an independent calibration of compressibility. An alternate non-invasive ultrasonic technique involves the measurement of blood flow in the carotid artery by ultrasonic exitation of the artery and determination of Doppler frequency shift.

Various types of ultrasonic ICP measurement techiques are disclosed in U.S. Pat. No. 3,872,858 to Hudson et al., U.S. Pat. No. 4,043,321 to Soldner et al., U.S. Pat. No. 4,971,061 to Kageyama et al., U.S. Pat. No. 4,984,567 to Kageyama et al., U.S. Pat. No. 5,388,583 to Ragauskas et al., U.S. Pat. No. 5,411,028 to Bonnefous, U.S. Pat. No. 5,617,873 to Yost et al. and U.S. Pat. No. 5,919,144 to Bridger et al. Such techniques involve the transmission of ultrasonic waves typically having frequences on the order 0.1 . . . 0.5 or 5.0 MHz into the intracranial media.

Each of the patents cited above is incorporated herein by reference.

Despite the above-noted attempts to develop non-invasive ICP measurement technique a need still exists for a non-invasive ICP measurement apparatus and method which can measure ICP absolute value and all possible ICP waves with skull penetration, which poses no health risks during long term monitoring and which is accurate enough. On the other hand, ICP changes are caused by intracranial media components volume changes. These components are arterial and venous blood, cerebrospinal fluid (CSF), brain tissues and intersticial fluid. For the targeted therapy of raised ICP it is necessary to know the volume of which intracranial component is increased. It is still impossible to identify which intracranial component is the cause of ICP increment applying known ultrasonic ICP measuring methods and apparatus. The need exists for an intracranial blood volume, CSF volume and brain parenchyma tissue volume simultaneous measurement and monitoring. The only known method and apparatus for the measurement of blood volume inside the brain parenchymal acoustic path is our Parent Patent: U.S. Pat. No. 5,388,583.

However, known ultrasonic non-invasive ICP measuring apparatus and methods are affected by the head external tissues blood flow phenomena, the phenomena of frequency dependent ultrasound velocity and attenuation inside the external tissues, skull bones and intracranial media. The accuracy of known methods is limited also by the instrumental drifts of the ultrasonically measured values.

The objectives of this invention are:

apparatus and method for simultaneous, real-time, in situ measurement and monitoring of intraparenchymal blood volume, brain parenchyma tissue volume and ICP, simultaneous, real-time and in situ measurement and monitoring of the ultrasonic pulses time-of-flight passing through the external tissues and skull bones, elimination of such measured data from the measured data of ultrasound time-of-flight through the human head and getting at the first time the measured data about the dynamics of ultrasound time-of-flight from the one internal surface of dura matter to the other internal surface. In this case the non-invasively measured time-of-flight dynamic data depend on intracranial media acoustic properties only and do not depend on the acoustic properties of external tissues and skull bones, simultaneous, real-time and in situ measurement and monitoring of the ultrasonic pulses internal period when these pulses are passing through the external tissues, skull bones and intracranial media, determination of the frequency dependent attenuation of the ultrasound inside the external tissues, skull bones applying measured internal periods data and elimination of such characteristics from the attenuation data of the ultrasound transmission through the human head. Again, this let us get at the first time the attenuation dynamics in intracranial parenchymal acoustic path only without the influence of external tissues and skull, simultaneous and real-time measurement of the time dependence of the instrumental delay of signal pulses in the circuits of transmitter, hybrid ultrasonic transducers, connecting cables and receiver, elimination of the instrumental delay from the measured data, identification and elimination of artefacts caused by ultrasonic transducers holder's—mechanical frame movement caused by the patients head movements.

The signals are displayed in the following sequence.

| Transmitted from left side of the human or animal head | Echo from the internal surface of dura mater of the left side of the head | Propagated through the parenchymal acoustic path and received on the right side of the head |
|---|---|---|
| Transmitted from right side of the human or animal head | Echo from the internal surface of dura mater of the right side of the head | Propagated through the parenchymal acoustic path and received on the left side of the head |

Figure 3:
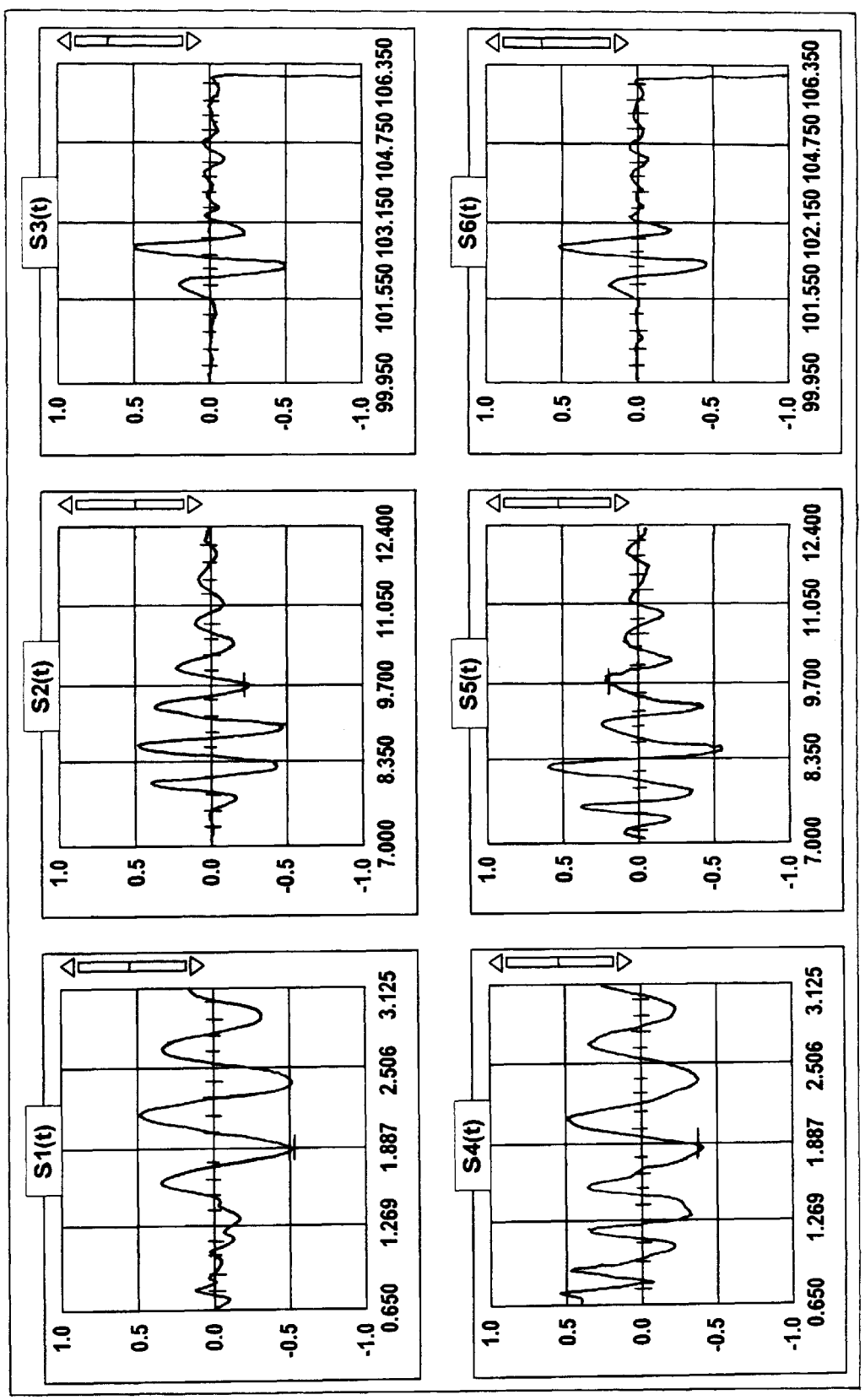
FIG. 3 is a virtual panel on the display of apparatus (FIG. 1A) for the displaying of all ultrasonic signals.
Figure 4:
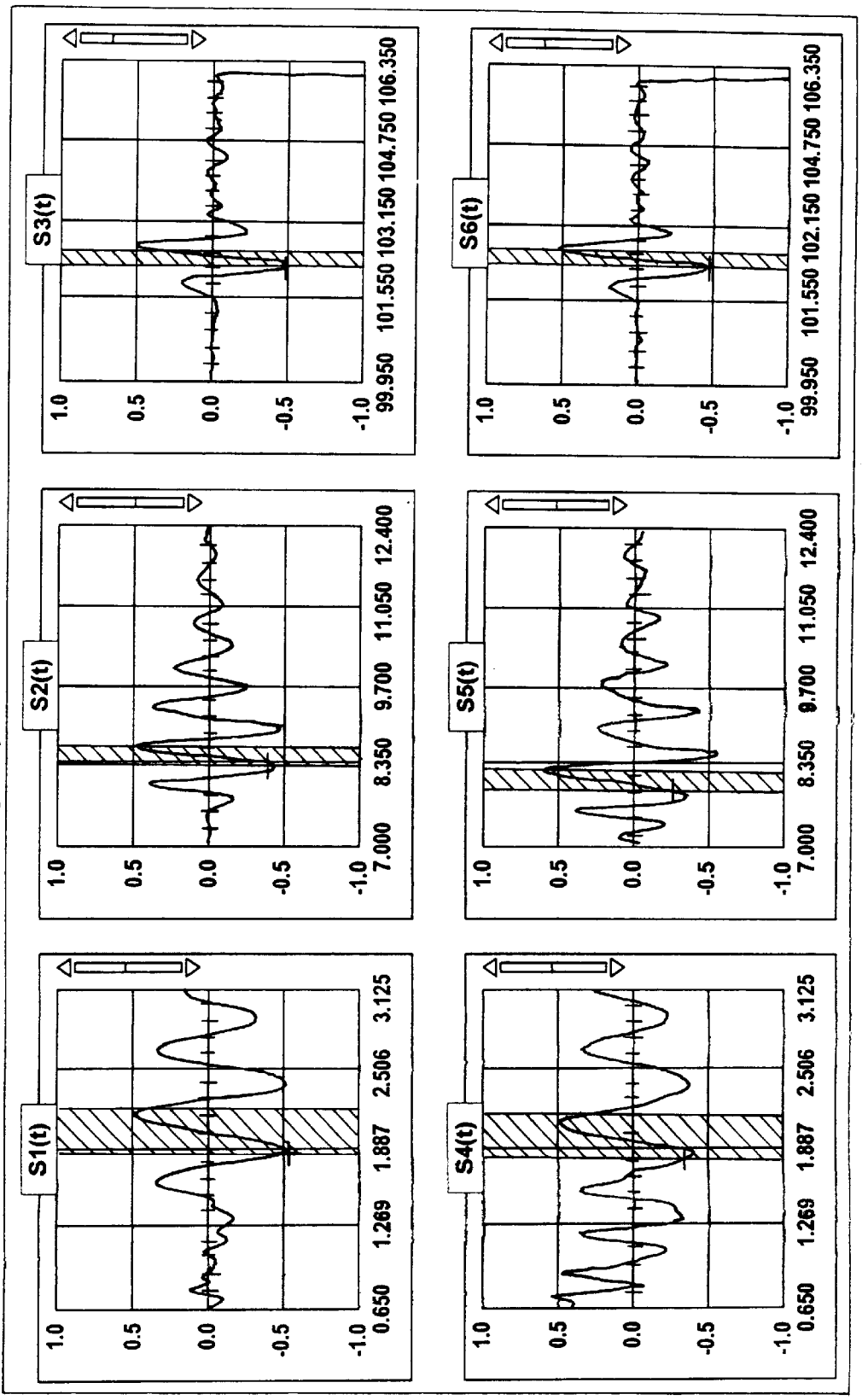

FIG. 4 is the same as in FIG. 3 but with the time windows for the signal zero crossing points time selection.

Figure 5:
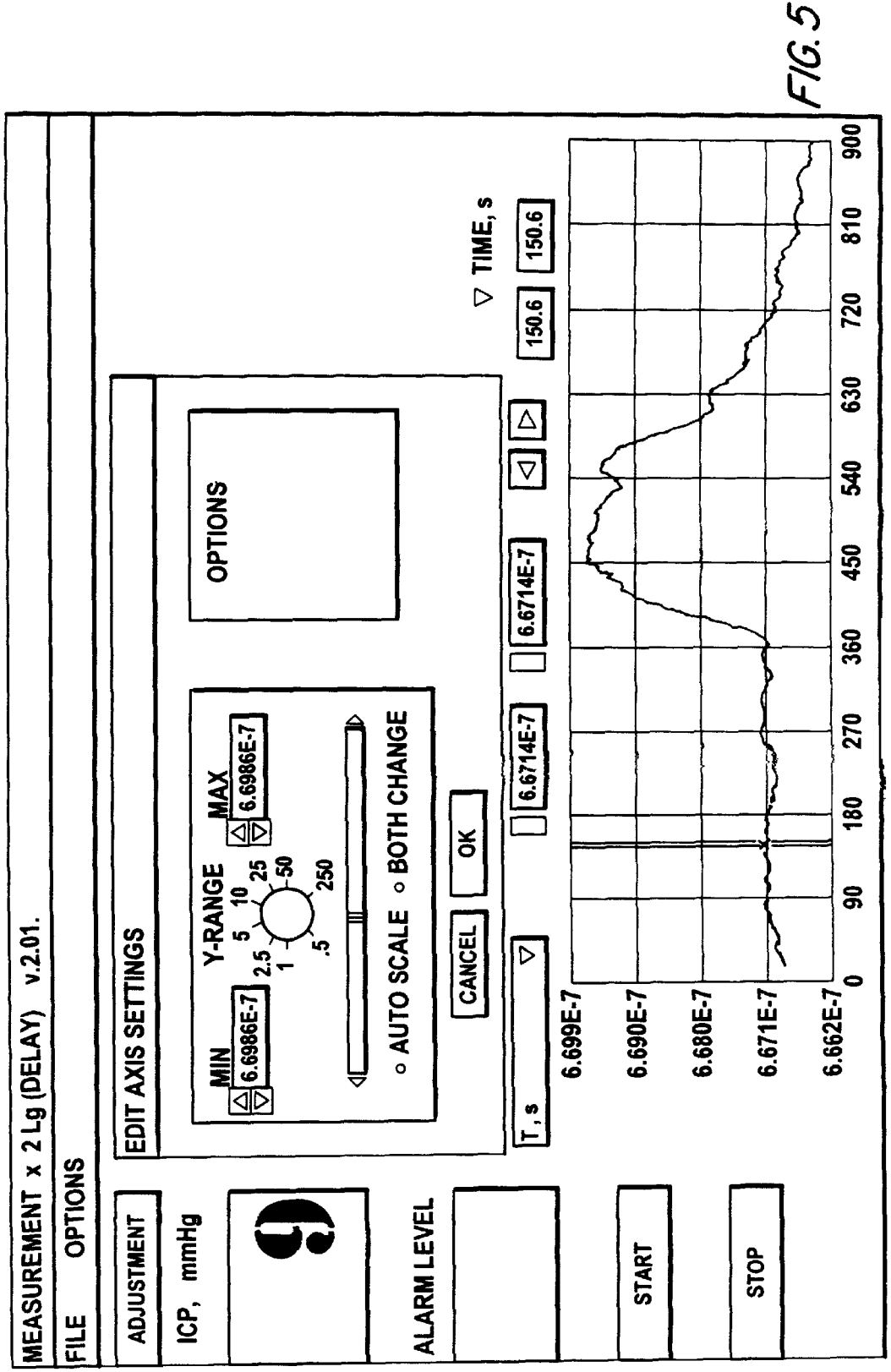

FIG. 5 is the virtual panel for the displaying of non-invasively measured ICP absolute value and the results of transintracranial time-of-flight monitoring. Here the marker shows the point of monitoring result when ICP was equal to 9.0 mmHg.

Figure 6:
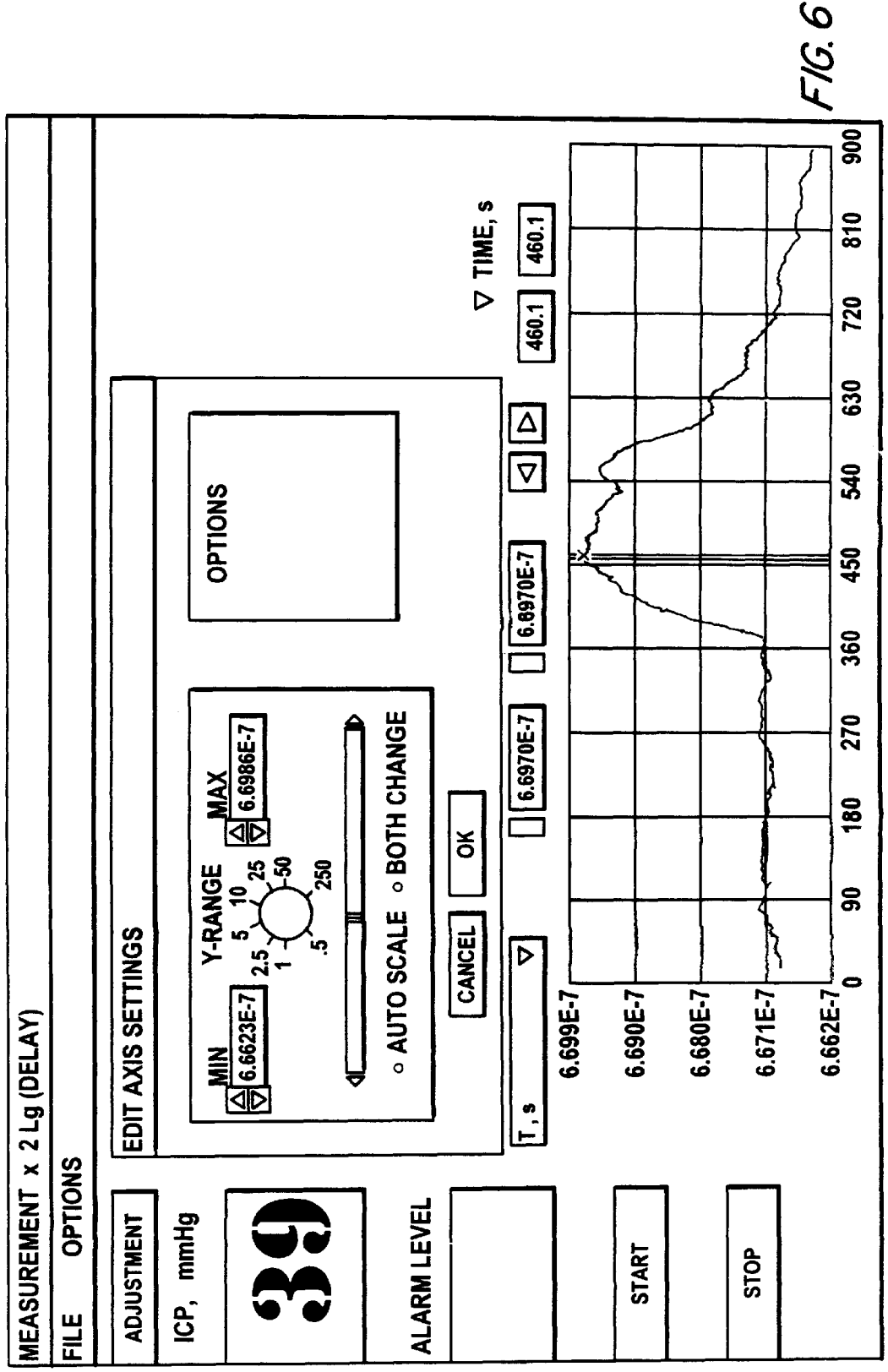

FIG. 6 is the same as in FIG. 5 but the marker shows ICP=39.0 mmHg.

Figure 1A:
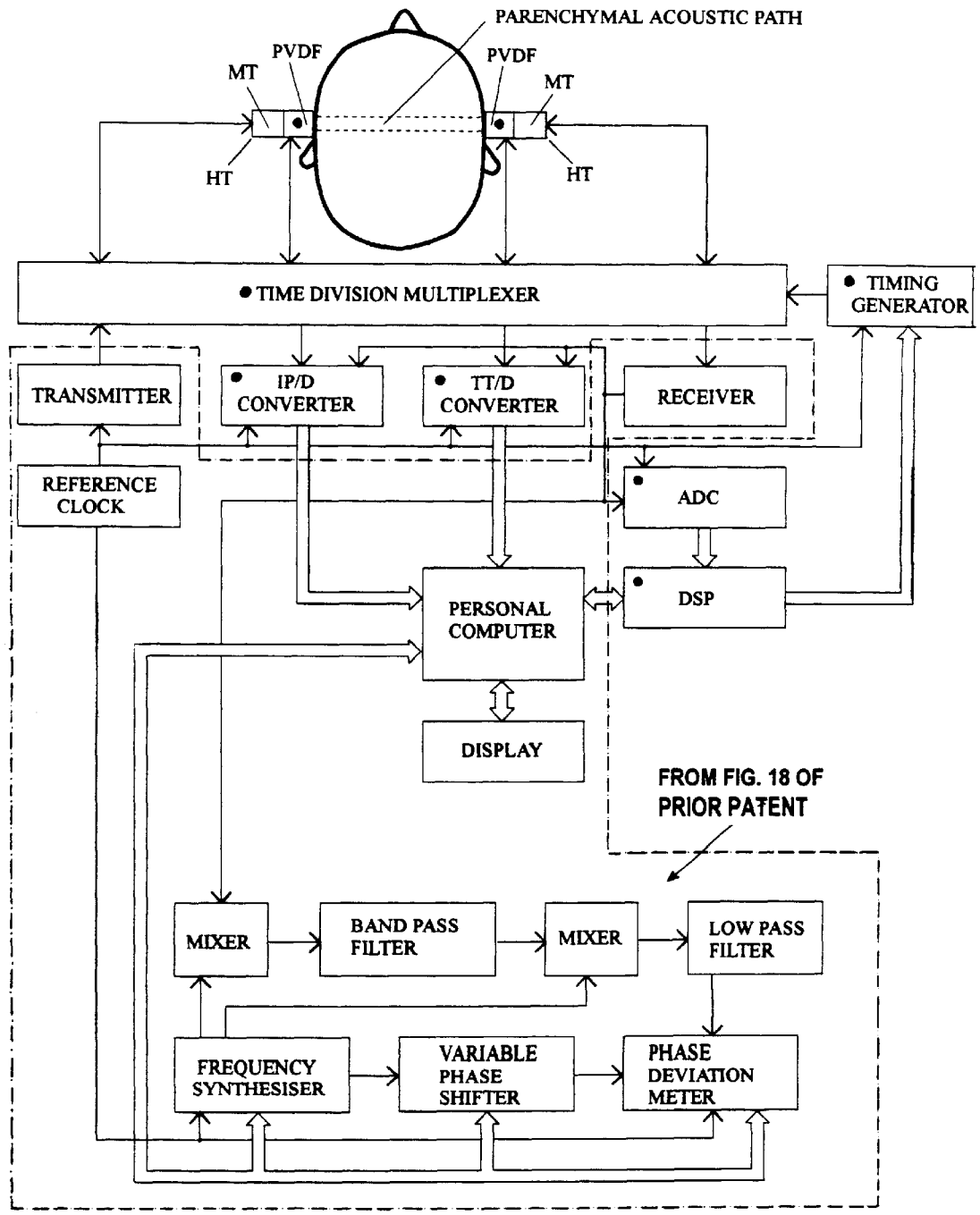
FIG. 1A is a schematic block diagram of an apparatus in accordance with the invention.
Figure 7:
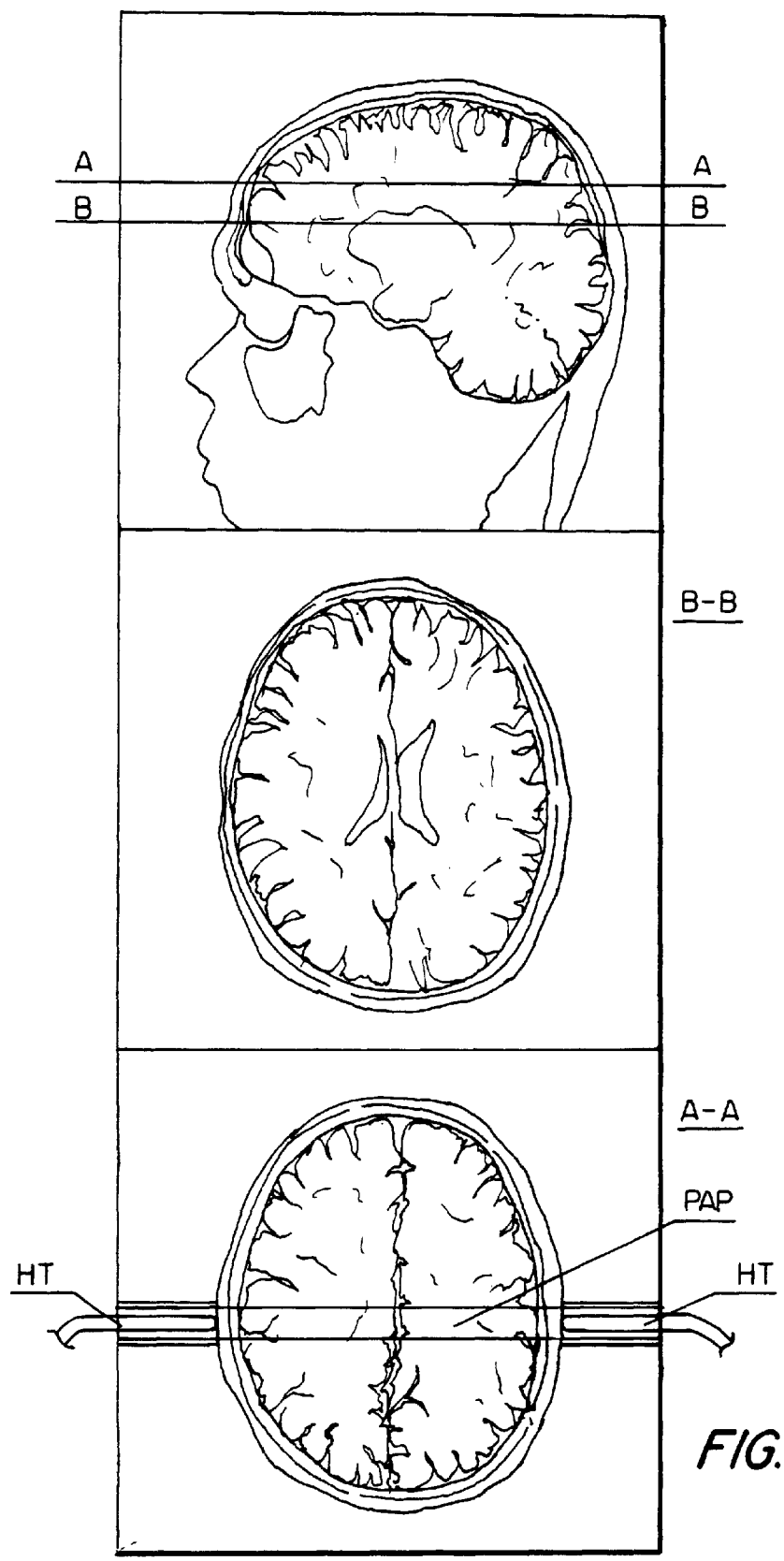

FIG. 7 is the MRI scan (A—A) of the parenchymal acoustic path without the cerebroventricles (shown in scan B—B) and without the relatively big cerebral blood vessels. Here HT—hybrid ultrasonic transducers (FIG. 1A).

Figure 8:
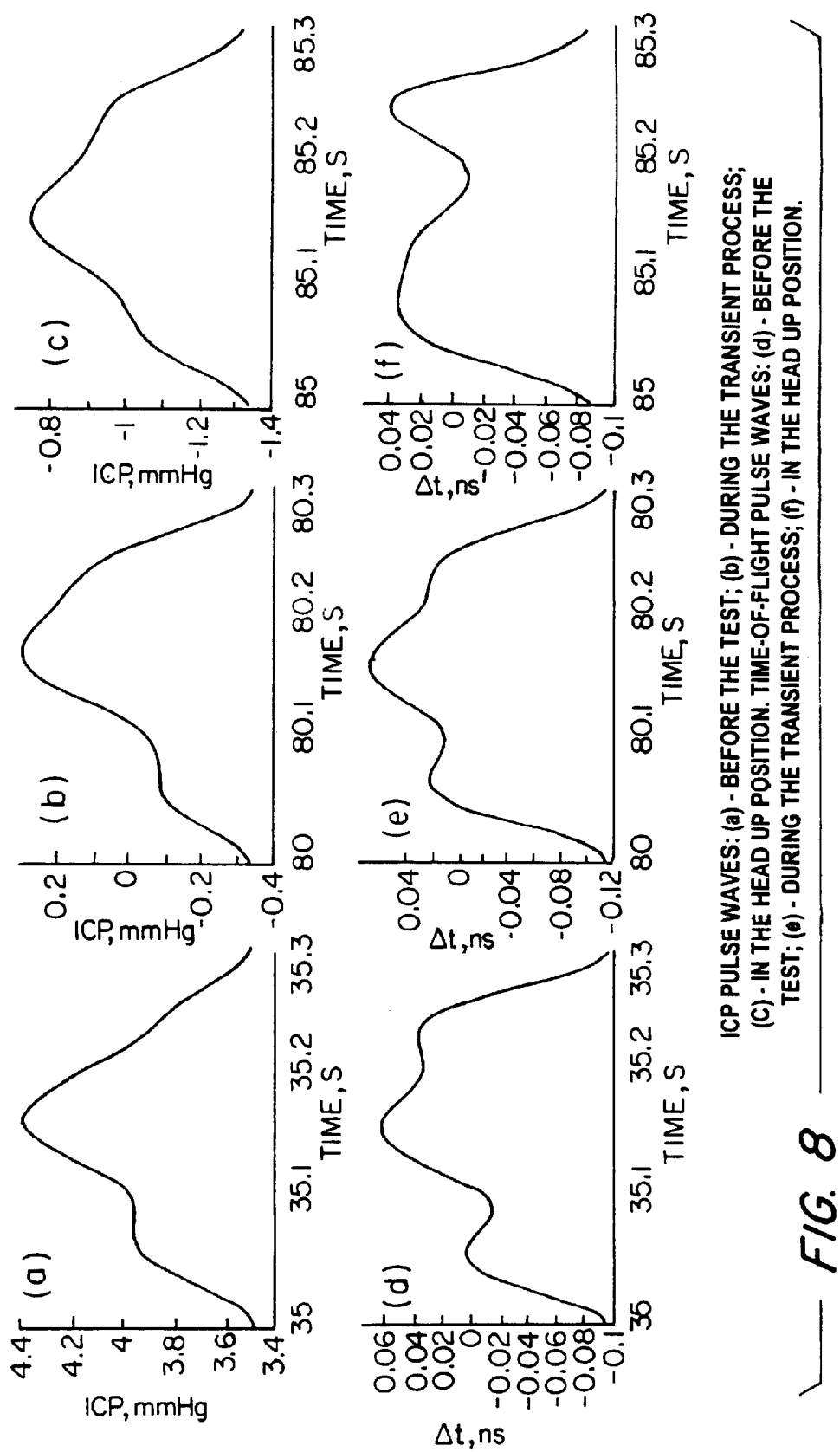

FIG. 8 are ICP pulse waves of piglet measured simultaneously using invasive ICP monitor (Camino Labs., USA) and non-invasive apparatus in accordance with the invention.

Figure 9:
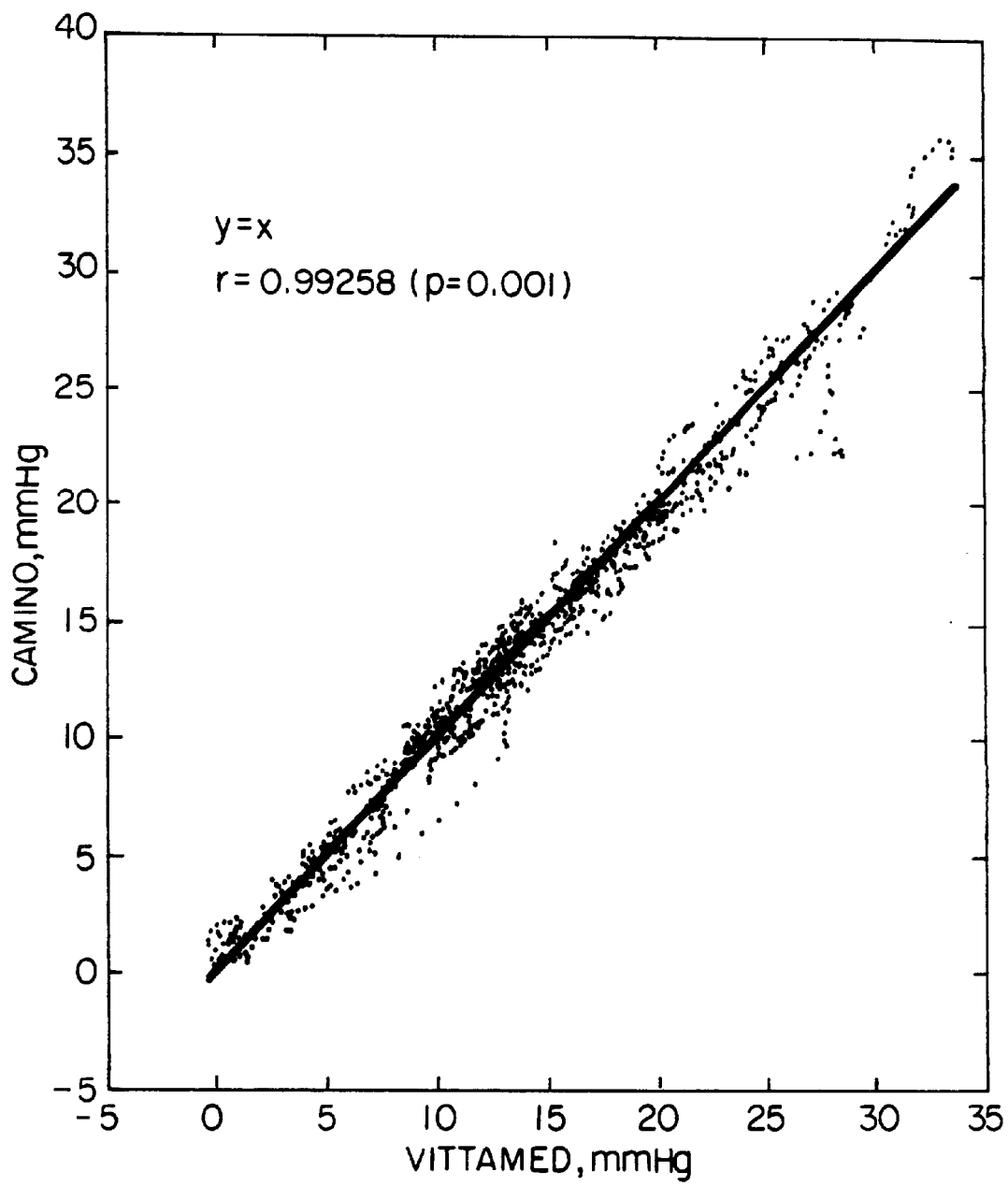

FIG. 9 is a linear plot of invasive ICP data versus simultaneously measured non-invasive ICP data for a group of 16 $CO_2$ tests (Table 2).

Figure 10:
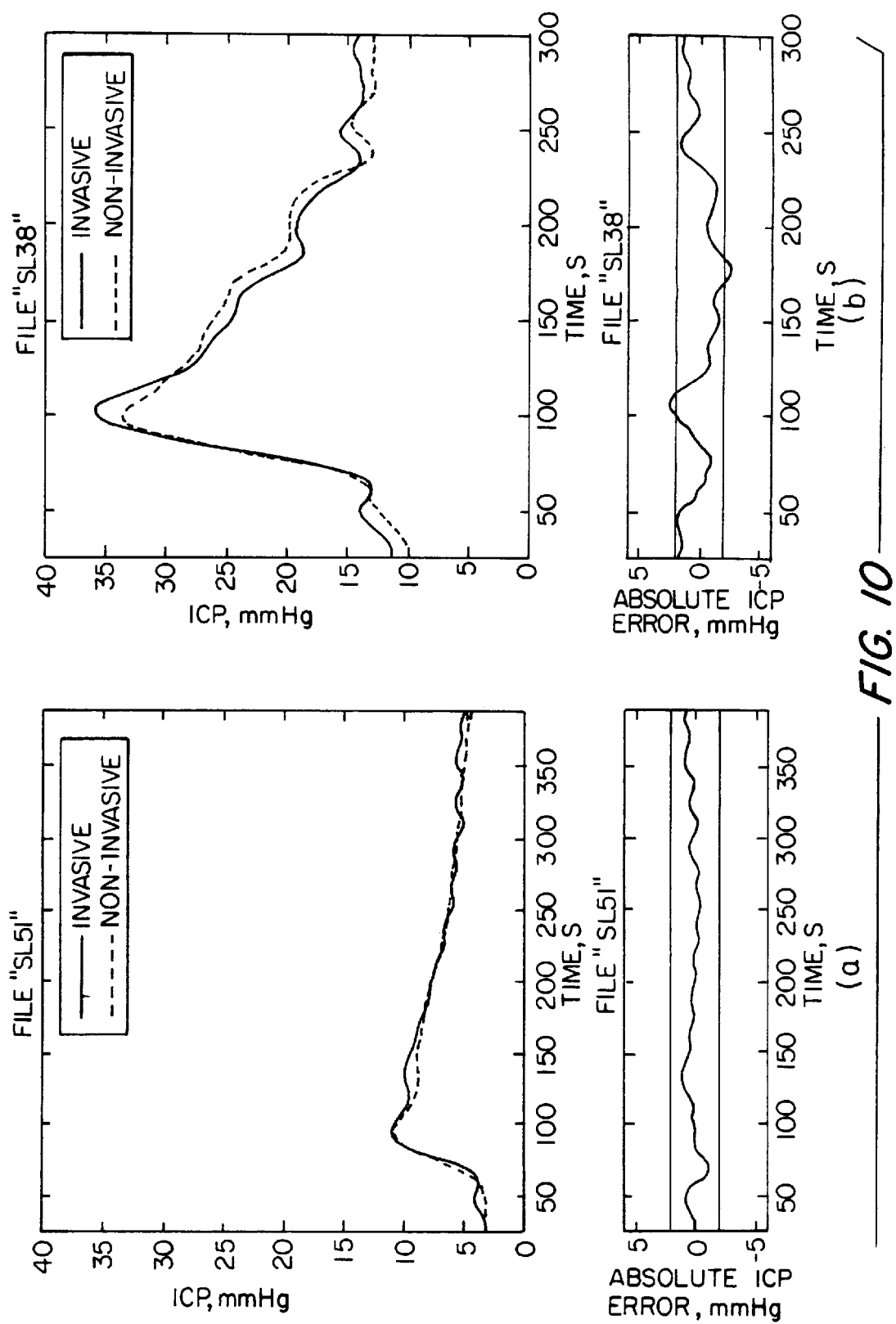

FIG. 10 is a comparison of invasive (Camino Labs., USA) and non-invasive ICP data during $CO_2$ vasoreactivity tests of two coma patients. The absolute dynamic errors (difference between invasive and non-invasive data) are shown in the lower graphs.

Figure 11:
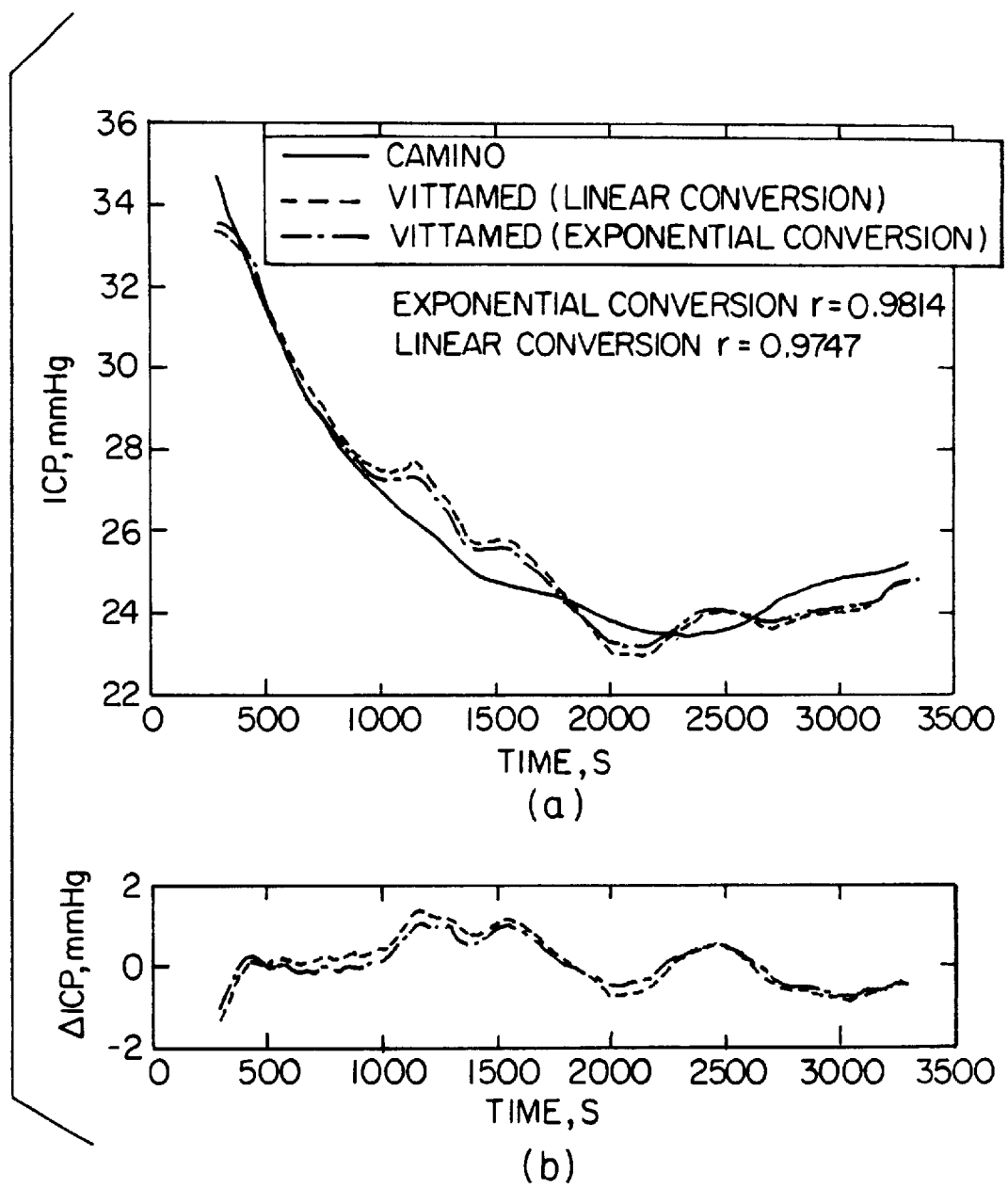

FIG. 11 is a comparison of invasive (Camino Labs., USA) and non-invasive ICP data during mannitol injection to the coma patient. The absolute dynamic error (difference between invasive and non-invasive data) is shown in the lower graph.

Figure 12:
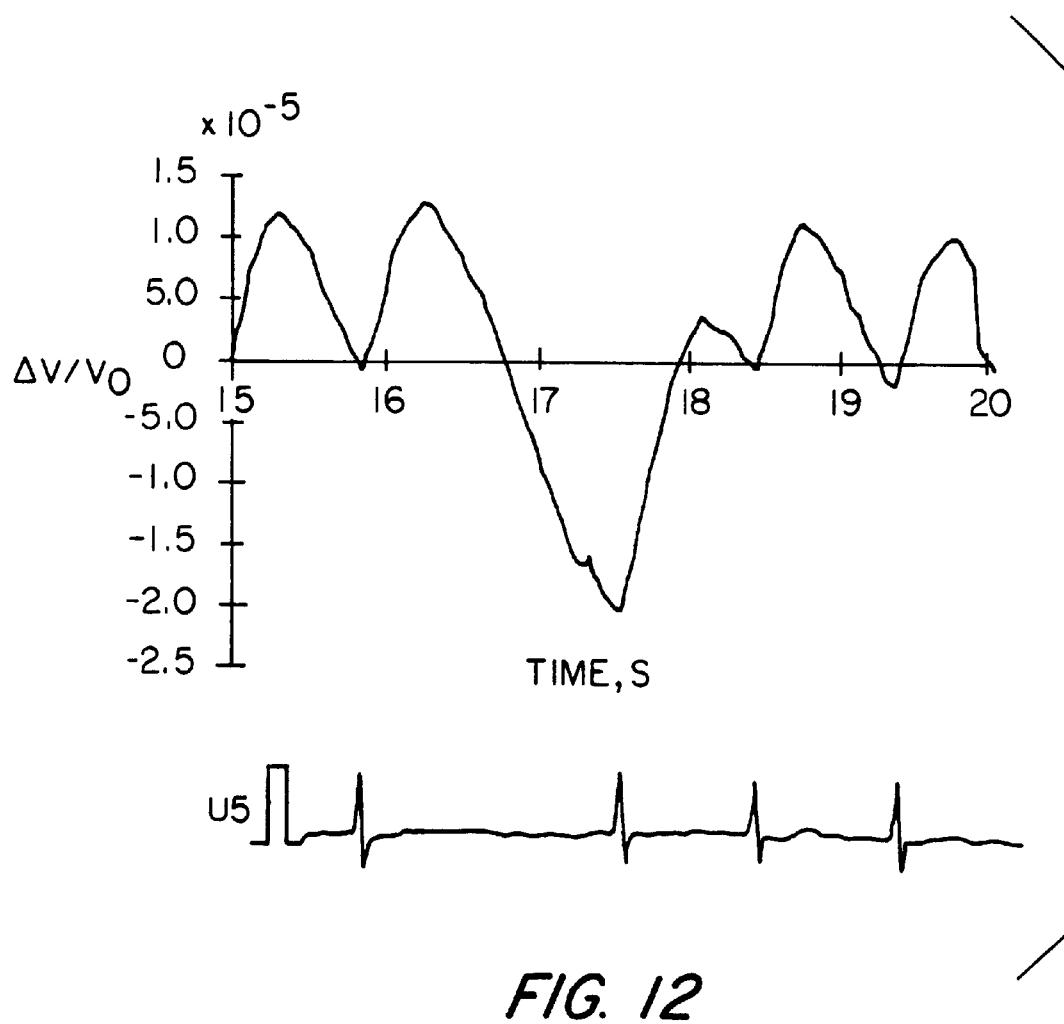

FIG. 12 is the non-invasively measured ultrasound velocity pulsation inside the parenchymal acoustic path of cardiological patient and simultaneously recorded ECG of this patient.

Figure 13:
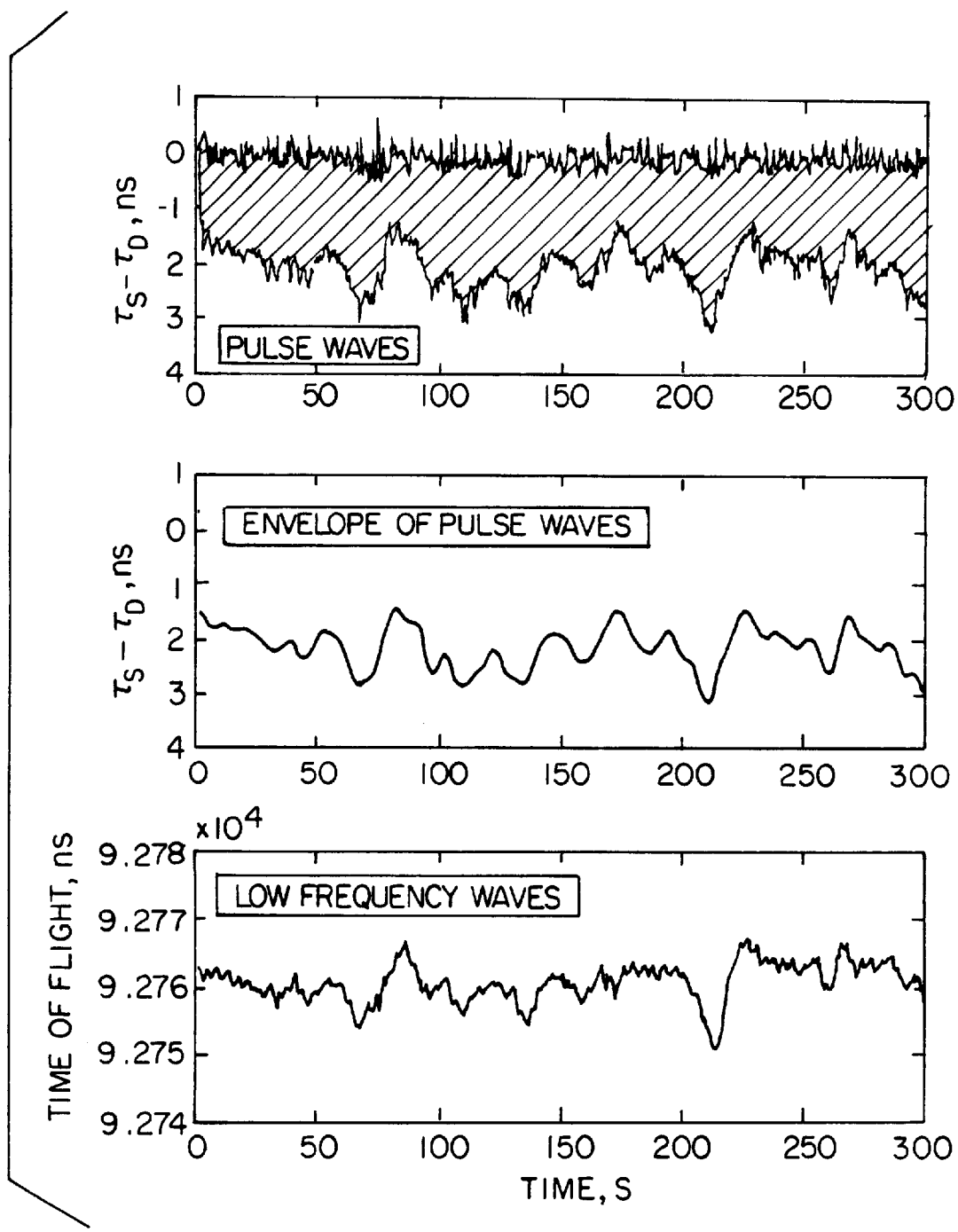

FIG. 13 are the simultaneously non-invasively recorded transintracranial time-of-flight pulse waves, the envelope of these waves and the slow time-of-flight waves.

Figure 14:
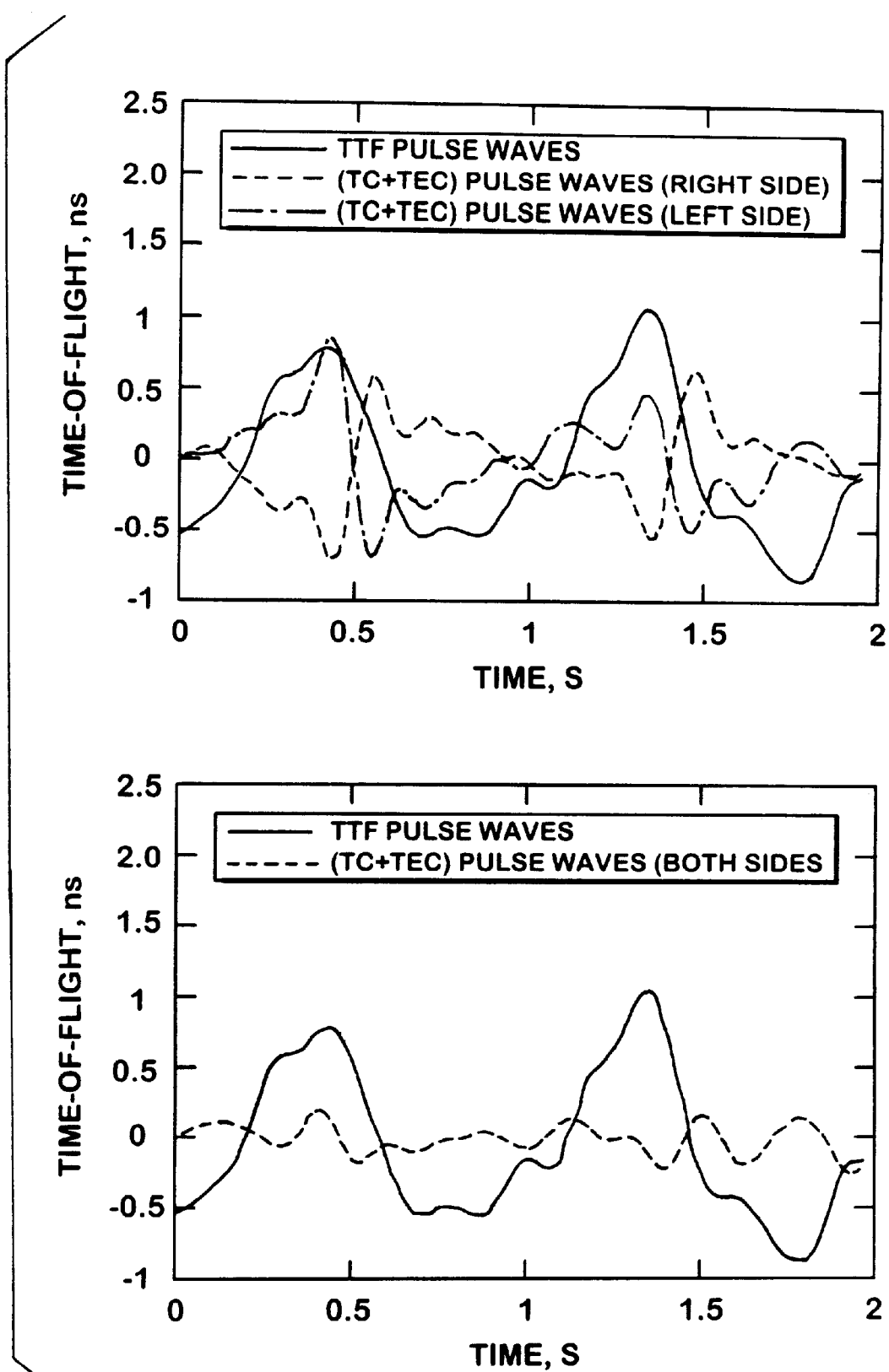

FIG. 14 are the simultaneously non-invasively recorded pulse waves of transintracranial time-of-flight (TTF) and transextracranial with transcranial time-of-flight (TC+TEC) on the both sides of human head in the case of free skull pulsation caused by ICP pulse waves.

Figure 15:
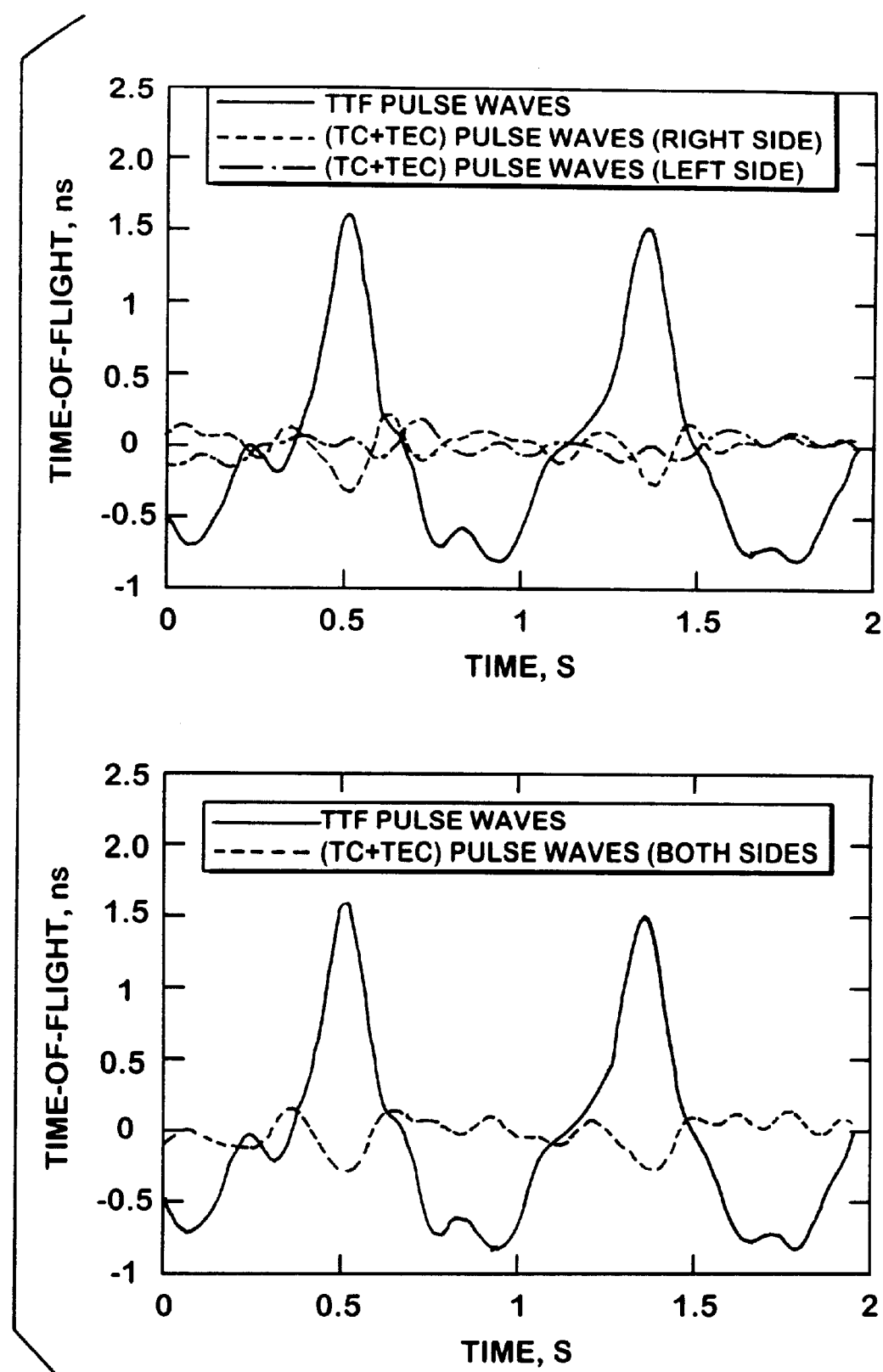

FIG. 15 is the same as in FIG. 14 when the skull pulsation is reduced because the hybrid ultrasonic transducers are pressed the external tissues and the skull.

SUMMARY OF THE INVENTION

The following hypotheses were postulated in our preliminary study:

a) Variations of acoustic properties of the human brain such as ultrasound attenuation and velocity are associated with the blood, cerebrospinal fluid or brain tissue volume changes.

b) These variations of acoustic properties of the human brain could be detected non-invasively and in real time.

We developed a new non-invasive technology for measuring the ultrasound velocity relative changes and ultrasound attenuation inside the parenchymal acoustic path crossing the human brain to confirm this hypothesis.

Our method is based on the transmission of short 2.0 MHz ultrasonic pulses from one side of the head and the receiving on the other side the ultrasonic pulses which were propagated through the external tissues, skull and intracranial media. We are detecting the ultrasound time-of-flight variations and ultrasound attenuation variations caused by the volume changes of intracranial media (cerebrospinal fluid, brain parenchyma tissue, arterial and venous blood) inside the parenchymal acoustic path. The acoustic properties of external tissues and skull are also measured separately by using echo method and the same ultrasonic signals as used for transmission through the human head. Their effects can thus be eliminated from the subsequent ICP and intracranial volume (ICV) calculations.

The acoustic properties of the cerebrospinal fluid (CSF), brain tissues, and blood are quite different. Their respective values have been experimentally determined and are listed in Table 1 below.

TABLE 1

Attenuation parameters and sound speed of the media, used for cranial simulation.

| Media | Attenuation parameters | | Sound speed c (m/s) | |
|---|---|---|---|---|
| | $\alpha_0$, dB/(cm MHz$^y$) | Y | Under (1.8 MHz, 37° C.) | References |
| Skull bone | 11.089 | 1.89 | 2652 | [1,2] |
| Blood | 0.212 | 1.27 | 1590 | [1,2] |
| Brain tissue | 0.869 | 1.07 | 1563 | [1,2] |
| CSF | 0.0023 | 1.99 | 1530 | [1,2,3] |

We found experimentally that if the distance $L_0$ between two hybrid ultrasonic transducers is fixed by mechanical frame and equal to constant it is possible to detect the ultrasonic signals time-of-flight changes inside the acoustic path. The acoustic path can cross different structures of the human head. In this case the ultrasound velocity relative changes caused by the volume changes of different intracranial compartments (cerebroventricles, blood vessels, cerebrospinal fluid compartments, parenchyma tissue volume) are equal to the measured time-of-flight relative changes.

A mathematical model was created for simulating the propagation of ultrasonic signal through the layered attenuating medium (human head) and dynamic physiological phenomena that cause changes of ICV and ICP.

If a broadband ultrasonic signal is propagating through a lossy dispersive medium, it is attenuated, delayed and the central frequency of a waveform is shifted down depending on media attenuation characteristics. Frequency dependent attenuation of biological tissues can be expressed by the power law function [1,4,5,6]:

$$\alpha(\omega) = \alpha_0 \omega^y, \quad (1)$$

where $\alpha_0$ and y are the tissue-dependent attenuation parameters. For many biological tissues an anomalous dispersion phenomenon is observed ($1 \leq y < 2$), i.e., higher frequency components of ultrasound pulse spectrum travel at higher phase speeds than lower frequency components. This phenomenon causes the modulation of central frequency. The output signal g(t) is the convolution of the input signal r(t) and the impulse response of the media h(t) [4,7,8]:

$$g(t) = r(t) \oplus h(t). \quad (2)$$

The impulse response is calculated by taking the inverse Fourier transform of the frequency response of the media:

$$h(t) = FT^{-1}[H(\omega)] = FT^{-1}[A(\omega)e^{-j\theta(\omega)x}] = FT^{-1}[e^{-\alpha(\omega)x}e^{jx\omega:V_p(\omega)}], \quad (3)$$

where $H(\omega)$ is the frequency response of the media, $A(\omega)$ is the magnitude function, $\theta(\omega)$ is the phase angle per units distance, x is the distance of the ultrasound travel, $V_p(\omega)$ is the phase velocity.

For simulating dispersion, attenuation and delay of an ultrasonic signal, a spectrum decomposition method was used [4,9]. Using this method a broadband ultrasonic signal is decomposed into narrowband components, and for each component a group delay, phase angle and attenuation parameter are calculated separately. To obtain the minimum reconstruction error, the Gaussian filters were chosen for decomposition [4]:

$$B_i(f) = \frac{1}{\pi} e^{-\left(\frac{f - f_L - (i-1)B}{B}\right)^2}, \quad i = 1, 2, \ldots, n \quad (4)$$

where $f_L = 0.6$ MHz is the center frequency of the lowest frequency filter, $f_H = 3.6$ MHZ is the center frequency of the highest frequency filter, $B = (f_H - f_L)/(n-1)$ is the filter bandwidth constant for all filters (B=0.3 MHz), n is the number of filters. The bandwidth of the filters B was chosen narrow enough so that the downshift of the signal center frequency in the i-th branch would be negligible [4].

For each decomposed narrowband component attenuation $a_i$ is calculated according to the equation (1), meanwhile the signal angular phase $\theta_i$ and group delay $t_{g\_}{}^i$ are defined as:

a) when y=1, a "nearly local model" developed by O'Donnel [10] is used. The signal angular phase and the group delay are:

$$\varphi_i = \frac{2\omega_i \alpha_0 x}{\pi}, \quad (5)$$

$$t_g = \frac{x}{V_g(\omega_i)} = \frac{x}{V_p(\omega_0)} - \frac{2\alpha_0 x}{\pi}\left(\ln\frac{\omega_i}{\omega_0} + 1\right), \quad (6)$$

b) when $1 < y \leq 2$, a "time.causal mode" proposed by Szabo [5] is used:

$$\varphi_i = -(y-1)\omega_i^y \alpha_0 x \tan\left(\frac{y\pi}{2}\right), \quad (7)$$

$$t_g = \frac{x}{V_g(\omega_i)} = \frac{x}{V_p(\omega_0)} - \alpha_0 x \tan\left(\frac{y\pi}{2}\right)\left(y\omega_i^{y-1} - \omega_0^{y-1}\right). \quad (8)$$

While developing a mathematical model of a human cranium it was assumed that the total head volume is 1600 ml that consists of 80% brain tissue, 10% cerebrospinal flow (CSF), and 10% blood [11]. The assumption was made that the ultrasonic signal propagates through the cranium 15 cm on a straight line and the thickness of cranial components according to the proportions presented above are 12 cm of brain tissue, 1.5 cm of CSF and 1.5 cm of blood, respectively. Also the thickness of a cranium bone is included and the total distance of signal propagation in the bone and in the external tissues is 1.6 cm.

Our computer modelling of ultrasound pulse propagation through the human head in which dynamic physiological phenomena (vasodilatation and vasoconstriction) occur shows that there are two ways of getting information about the changes of craniospinal volume or ICP. The change of ICP is related to the deviation of a craniospinal volume. Simulated physiological phenomena show, that in vasodilatation cases, the increase of the brain blood volume inside the acoustic path within the physiological limits causes a decrease of the received ultrasonic signal's first period and the signal propagation time. The increase of brain tissue volume and the decrease of CSF volume inside the acoustic path cause the increase of the ultrasonic signal's first period and the decrease of the signal's time-of-flight. The dependence of both the deviation of the signal time-of-flight and the deviation of the first period on the craniospinal volume deviation is linear (with the error less than +/−1%) in the investigated pathophysiological range of craniospinal volume changes from 0 ml to 20.0 ml and ICP changes from 10.0 mmHg until 80.0 mmHg. Modelling also shows that the pathophysiological variations of the cerebral blood or parenchyma tissue volume inside the acoustic path and ICP are detectable if our non-invasive technique is used. Modelling also shows that it is possible to eliminate the acoustic properties of external tissues, skull and dura mater and also eliminate the possible Doppler shift in real-time applying the echo method, the fast commutation (500 Hz) of signal transmission direction and the same ultrasonic signals. In this case the special ultrasonic transducers for such purposes need to be created and the digital signal processing technology of ultrasonic signals need to be introduced into our monitors.

Figure 1B:
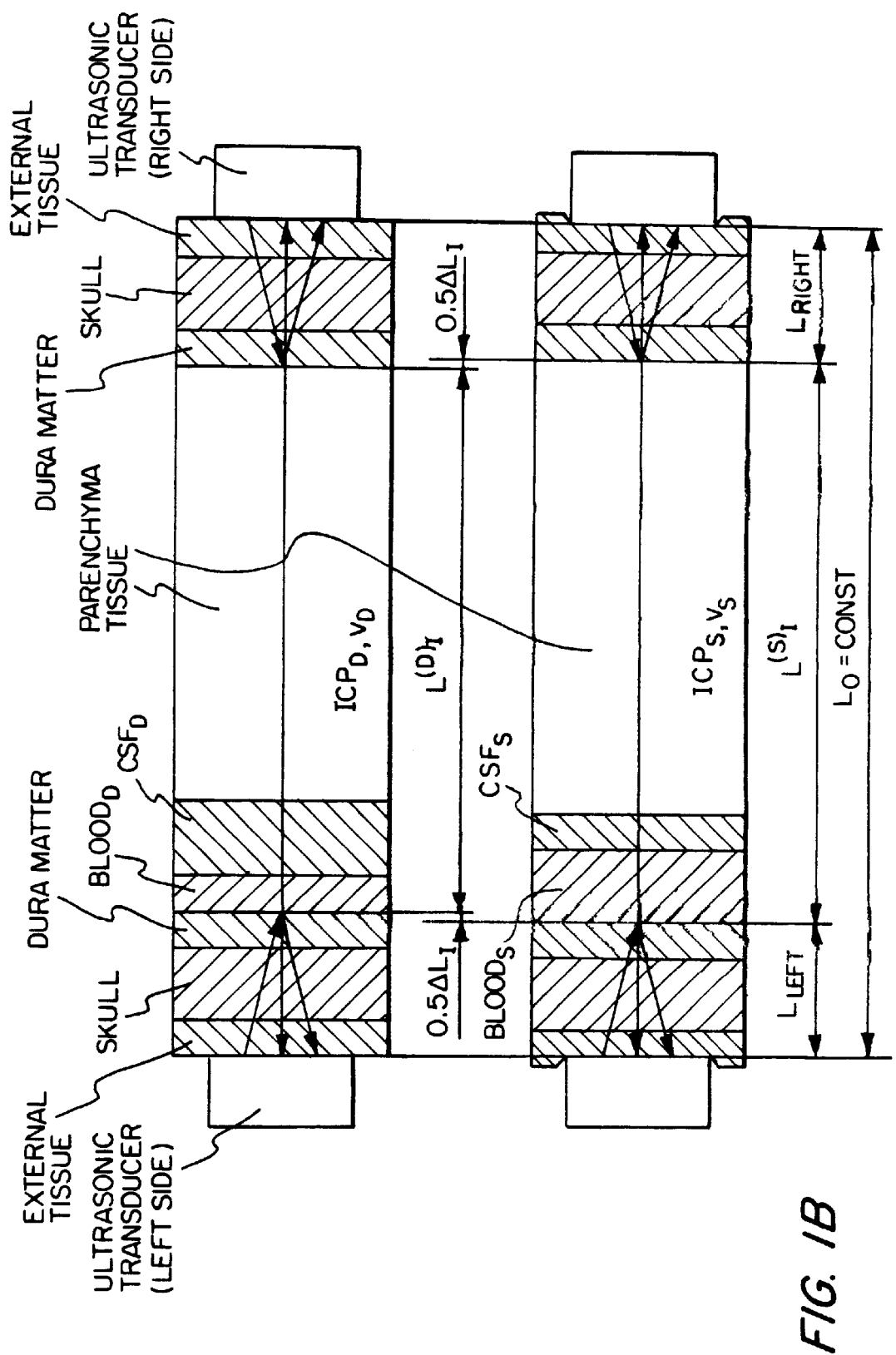
FIG. 1B is a diagram of the internal structure of parenchymal acoustic path in accordance with the invention: upper diagram is at diastolic moment of cardiac pulsation, lower diagram is at systolic moment of cardiac pulsation.
Figure 2A:
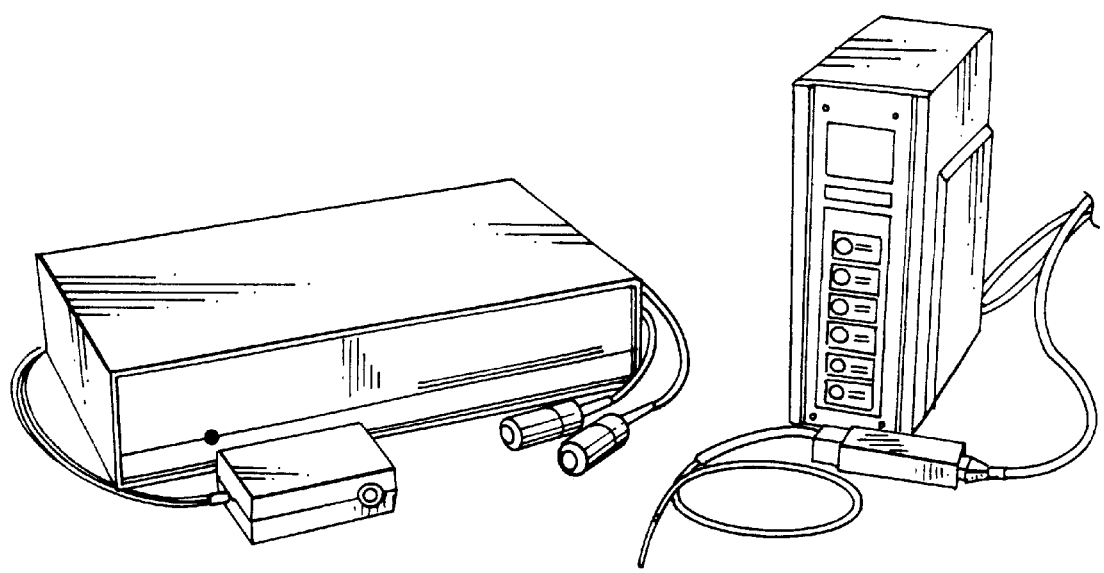
FIG. 2A is a general view of electronic block with hybrid ultrasonic transducers of an apparatus shown in FIG. 1A in accordance with the invention comparing with invasive ICP monitor (Camino Labs., USA).
Figure 2B:
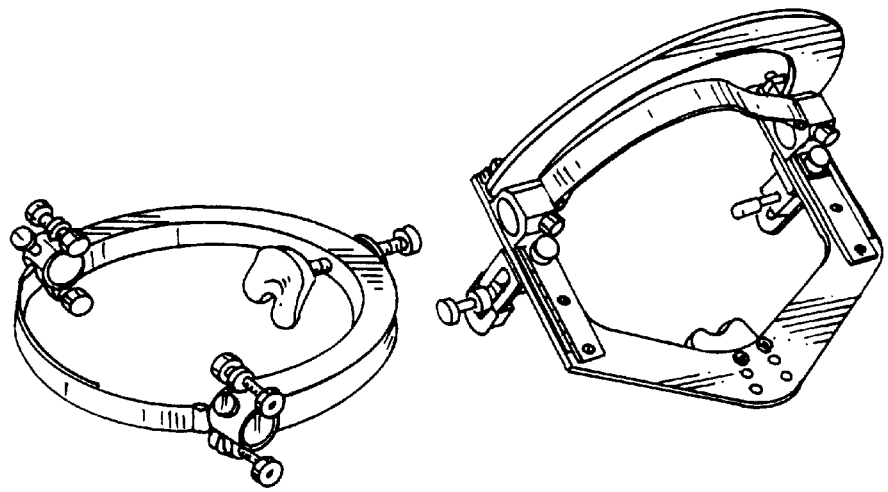
FIG. 2B is a view of mechanical frames for holding and fixation of hybrid ultrasonic transducers on the patient head.

The apparatus (FIG. 1A) consists of PC, electronic block, two ultrasonic transmitting/receiving transducers and mechanical frame for the fixation of ultrasonic transducers on the patient head. FIG. 1B is a diagram of the internal structure of parenchymal acoustic path in accordance with the invention. The upper diagram of FIG. 1B illustrates the internal structure in the diastolic moment of cardiac pulsation and the lower diagram computer shown in FIG. 1A. The general view of electronic block with ultrasonic transducers of non-invasive monitor is compared with invasive fiber optic ICP monitor (Camino Labs., USA) on FIG. 2A. The view of mechanical frame is shown on FIG. 2B. The virtual panels of non-invasive monitor are shown on FIGS. 3, 4, 5, 6.

Each hybrid ultrasonic transducer (HT) (FIG. 1A) consist of the main 2.0 MHz wide band ceramic ultrasonic transducer (MT) and super wide band (the bandwidth is more than 10.0 MHz) polyvinylidene fluoride piezoelectric film (PVDF) ultrasonic transducer. The PVDF transducer is placed between the human head and the main ultrasonic transducer. This combination is called as the hybrid transducer HT (FIG. 1A). In this case the ultrasonic pulses transmitted by the main transducer pass through PVDF transducers practically without the attenuation. At the output of PVDF transducer in this case we have electric pulses—copies of transmitted ultrasonic pulses (FIG. 3A and FIG. 4A), copies of the ultrasonic echo pulses which pass twice the external tissues, skull bones and dura matter (FIG. 3B and FIG. 4B). These ultrasonic pulses are received by PVDF transducers on the both sides of the human head because of the time division multiplexing of ultrasonic pulses transmission directions. These directions are changed to the opposite by the time division multiplexer (FIG. 1A) 500 times per second. The period of the human head insonation is fixed by reference clock (FIG. 1A) and is equal to 1000 Hz. The time-of-flight determination errors caused by frequency dependent ultrasound velocities in the external tissues, skull and intracranial media are eliminated because of including super wide band PVDF transducers into hybrid ultrasonic transducers and because of application of the signals with the same spectrum for propagation through the human head and for propagation through the external tissues and skull applying echo method. Known methods for simultaneous measurement of time-of-flight in external tissues, skull bone and dura matter together with time-of-flight measurement in the human head are based on frequency division multiplexing of echo channel and direct transmission channel. It is impossible to eliminate the errors caused by frequency dependent ultrasound velocities when different frequency ultrasonic signals are used in the known cases.

The parenchymal acoustic path (PAP) (FIG. 7) is used for the human head insonation. This path (FIGS. 7A—A) cross the brain parenchyma tissue without the cerebroventricles (FIGS. 7B—B) and relatively big cerebral vessels inside. The brain blood volume inside this path depends on the state of dilation or constriction (or the cerebral blood flow autoregulation state) of the brain arterioles and aucillary vessels and on the state of (compression by ICP of the brain venules and bridging veins. This brain blood volume is determined measuring the transintracranial time-of-flight (TTF) of ultrasonic pulses propagated through the intracranial media. The TTF changes mainly depend on the brain blood volume because the ultrasound velocity $v_B$ is bigger in the blood comparing with the ultrasound velocity $V_{PT}$ in the brain parenchyma tissue and the ultrasound velocity $V_{CSF}$ in the cerebrospinal fluid (Table 1).

Intracranial parenchyma volume changes are determined by the measurement of internal period (IP) of ultrasonic pulses propagated through the intracranial media because the parenchyma tissue volume occupies more than 80% of the parenchymal acoustic path total volume. The attenuation of ultrasound in the parenchyma tissue (Table 1) is much bigger than in the blood or CSF.

The main technical parameters of our PC based apparatus is: central frequency of transmitted ultrasonic pulses spectrum—2.0 Mz duration of transmitted ultrasonic pulses 800 ns at the level 0.5 of envelope and its repetition frequency 1.0 kHz, acoustic output parameters: derated spatial-peak, temporal-average intensity $I_{SPTA3}$=25+/−2.2 mW/cm$^2$ derated spatial-peak, pulse-average intensity $I_{SPPA3}$= 1+/−0.09 W/cm$^2$; ultrasonic power $W_o$=1.8 mW, resolution of measured time-of-flight or ultrasound velocity relative values 1.25E-6 at the bandwidth of non-invasive intracranial pressure/volume pulse waves measuring channel from 0 Hz until 12 Hz, resolution of measured intracranial parenchyma volume changes inside the parenchymal acoustic path less than 0.5% within all physiological region of standard intracranial pressure/volume relationship.

This non-invasive apparatus has virtual panels for pulse, respiratory and Lundberg's ICP waves and slow ICP/ICV trends monitoring (FIGS. 5, 6). The absolute ICP value is calculated by applying knowledge-based conversion of non-invasively measured ultrasound time-of-flight and attenuation data and displayed in the separate window (FIGS. 5, 6).

Figure 1C:
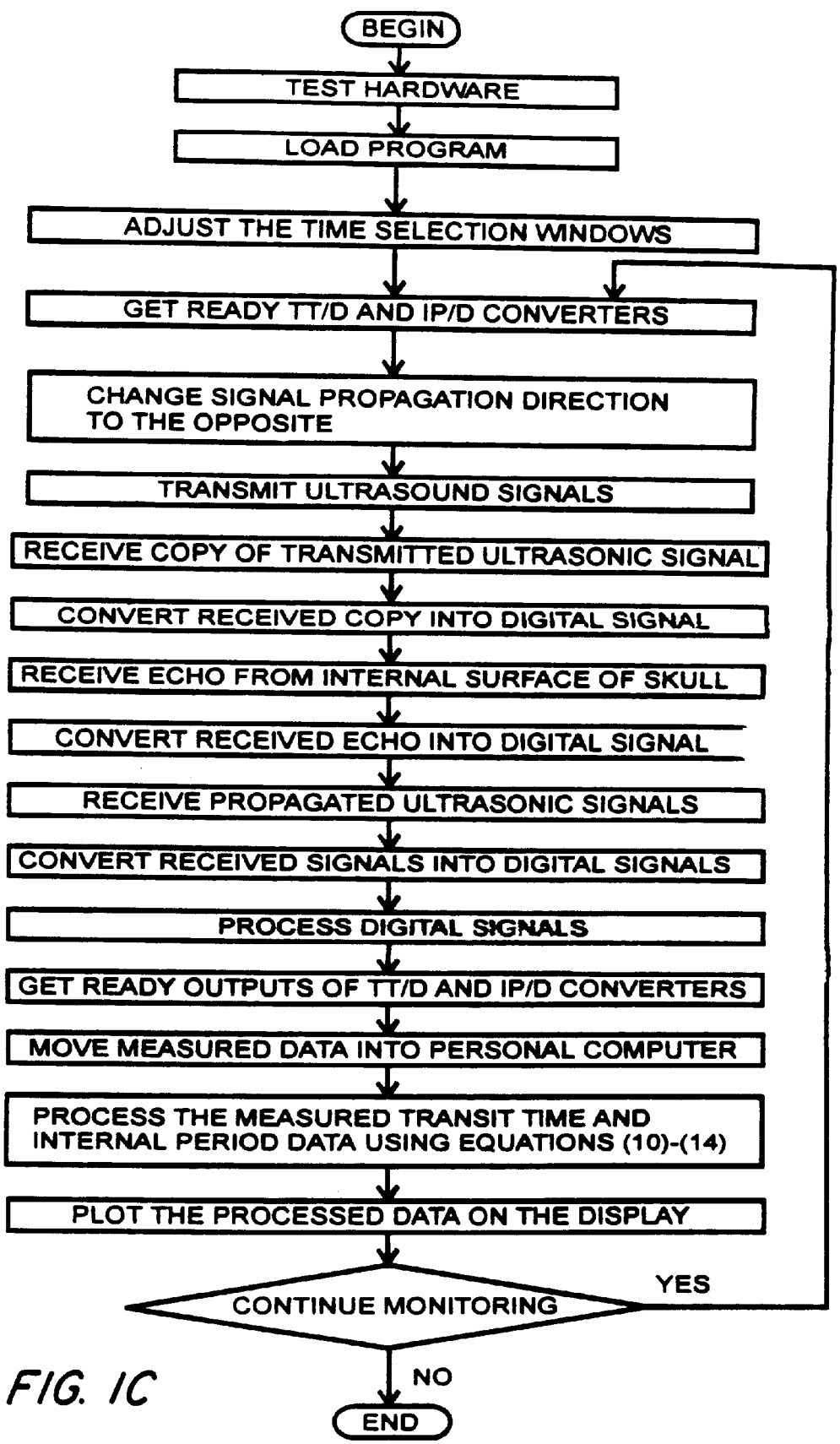
FIG. 1C is a flow chart for the program steps for the computer shown in FIG. 1 A.

The operation of apparatus (FIG. 1A) is illustrated in FIG. 1B. The algorithm of operation is given in FIG. 1C.

The following abbreviations are used in FIG. 1B: Blood$_D$—total diastolic blood volume inside the parenchymal acoustic path, CSF$_D$—total diastolic CSF volume inside the same path, $ICP_D$—diastolic value of ICP pulse wave, $v_D$—diastolic value of ultrasound velocity in the parenchymal acoustic path, $L^{(D)}_I$—diastolic value of the distance between internal surfaces of dura matter. $\Delta L_I = L^{(S)}_I - L^{(D)}_I$, $L_0$—the constant distance between the ultrasonic transducers fixed by mechanical frame—ultrasonic transducers holder. The subscripts S in FIG. 1B mean the systolic values.

It follows from FIG. 1B that systolic blood volume is increased comparing with diastolic blood volume, systolic CSF volume is decreased and parenchymal tissue volume is almost not changed inside the parenchymal acoustic path. CSF volume is decreased because of the CSF pulsatile outflow into the spinal channel. It is also possible that the systolic intracranial distance $L^{(S)}_I$ can be a little bit bigger than the diastolic distance $L^{(D)}_I$ because of the skull displacement caused by systolic ICP increment ($ICP_S > ICP_D$). It follows from FIG. 1B that in case of systole $v_S > v_D$ because the ultrasound velocity in the wider blood layer is bigger than in the diastolic case. The result is that systolic time-of-flight $TTF_S$ is less than diastolic $TTF_D$. The other result is that the amplitude of TTF pulse wave caused by ICP pulse wave will be negative. The amplitude of TTF pulse wave is determined as $TTF_S - TTF_D$.

From FIG. 1B also follows that the time-of-flight through external tissues (TEC), skull bones and dura matter (TC) is measured applying echoes from the internal surface of dura matter on the left and right sides of the human head. The transintracranial time-of-flight (TTF) can be determined in this case as $$TTF = TF - (TEC+TC)_R - (TEC+TC)_L - T_0, \quad (9)$$

where TF is the time-of-flight between left and right hybrid ultonic transducers (FIG. 1B), $T_0$—instrumental delay time of signals in the circuits of transmitter, connecting cables, hybrid ultrasonic transducers and receiver (FIG. 1A). In our method the echo method is used and echo signals are received after two times propagation through the external tissues, skull bones and dura matter. Also the direction of propagation between two ultrasonic transducers is periodically inverted. That is why in our method the TTF is calculated in the personal computer as:

$$TTF = 0.5(TF_1 + TF_2) - 0.5(2(TEC+TC)_R + 2(TEC+TC)_L) - 0.5(T_{o1} + T_{o2}), \quad (10)$$

here subscrips 1 and 2 mean the opposite directions of ultrasound propagation. All time-of-flight values are measured in real time by time-of-flight to digit converter (TT/D, FIG. 1A). To measure these values the time windows are used for every single pulse (FIG. 4). These time windows are used for the selection of the same zero crossing point of signal functions where the slope of signal function is maximal (FIG. 4). The width of time selection windows is chosen less than the half of every signals' internal period (IP). Only one zero crossing point of signal function is selected for time-of-flight measurements in this case. In the case of internal period (IP) measurement the separate internal period to digit (IP/D) converter is used (FIG. 1A). The real time time-of-flight and internal period simultaneous measurement data are transmitted to the personal computer (FIG. 1A) for the filtering, calculations, displaying and saving.

The instrumental delay times $T_{01}$ and $T_{02}$ are measured in real time periodically connecting the outputs of left and right PVDF transducers by time division multiplexer (FIG. 1A). In this case the object of measurement—parenchymal acoustic path is eliminated from the time-of-flight measurement channel and only $T_{01}$ and $T_{02}$ are measured by TT/D converter. The measured data are used for calculation of TTF data by formula (10). All instrumental drifts of delay times of apparatus (FIG. 1A) are automatically eliminated in this case.

The ultrasound intracranial attenuation inside the parenchymal acoustic path can not be measured applying convenient methods. First of all, it is impossible to get the necessary time resolution applying fastest and highest resolution analog to digital converters (ADC FIG. 1A) and digital signal processors (DSP FIG. 1A). That is why in our apparatus the IP/D converter is used to measure the internal period of ultrasonic signals with super high resolution up to 60 ps. The amplitude of transmitted signal, echo signals and propagated through the human head signals is determined applying ADC, DSP and the averaging up to 5000 pulses. The ultrasonic signals are virtually reconstructed in the personal computer applying the measured data of internal period and amplitude and also applying the Gaussian shape of the signals envelope.

The elimination of the frequency dependent attenuation in the external tissues and skull bones $\beta_L(j\omega)$ of the left side of the head and the right side of the head $\beta_R(j\omega)$ from the total attenuation data $\beta_T(j\omega)$ is carried out using the following formulas:

$$S_{EL}(j\omega) \times (\beta_{IL}(j\omega))^2 = S(j\omega), \quad (11)$$

$$S_{ER}(j\omega) \times (\beta_{IR}(j\omega))^2 = S(j\omega), \quad (12)$$

$$S_T(j\omega) \times \beta_{IT}(j\omega) = S(j\omega), \quad (13)$$

where $S(j\omega)$—complex spectrum of the transmitted ultrasonic signal, $S_{EL}(j\omega)$—complex spectrum of the echo signal from the left internal surface of dura matter, $S_{ER}(j\omega)$—the same for the right side, $S_T(j\omega)$—complex spectrum of the signal which passed the human head, $\beta_{IL}(j\omega)$—complex transient function of the filter which is inverse to the frequency dependent attenuation function $\beta_L(j\omega)$ of the left side of cranium with external tissues, $\beta_{IR}(j\omega)$—the same for the right side, $\beta_{IT}(j\omega)$—the same for the human head, all inverse filters market by (I*) have the complex transient function $\beta_{I^*}(j\omega) = 1/(\beta \cdot (j\omega))$, were $\beta \cdot (j\omega)$ is the attenuation function of structure layer (*).

The frequency dependent transcranial attenuation of ultrasound $B_{TTC}(j\omega)$ from the left internal surface of dura matter to the right internal surface of the dura matter is calculated from.

$$\beta_{TTC}(j\omega) = (\beta_{IL}(j\omega) \times \beta_{IR}(j\omega))/\beta_{IT}(j\omega) \quad (14)$$

The functions $\beta_{IL}(j\omega)$, $\beta_{IR}(j\omega)$, $\beta_{IT}(j\omega)$ are calculated in the personal computer applying formulas (11), (12), (13), measured results of internal periods of signals $S(j\omega)$, $S_{EL}(j\omega)$, $S_{ER}(j\omega)$ and $S_T(j\omega)$, virtually reconstructed time dependencies of these signals and fast Fourier transform (FFT). The determined value of $\beta_{TTC}(j\omega)$ is linearly proportional to the parenchyma tissue volume inside the parenchymal acoustic path.

Animal Study. Using the apparatus we investigated the hemodynamic responses of piglets cerebral parenchyma to body tilting, Queckenstedt and $CO_2$ reactivity tests. Ten piglets were studied. They were anesthetized, intubed and artificially ventilated. Invasive (Camino Lab., USA) and our non-invasive ICP monitors were used simultaneously during the experiments. Blood gas analysis was also conducted. A parenchymal acoustic path was used for non-invasive measurements and the time dependencies of ultrasound velocity and attenuation were measured. The measured data were compared with simultaneously recorded invasive ICP data.

There was a significant correlation between invasively and non-invasively measured ICP data for all ten test subjects (r=0.84 . . . 0.98, p<0.001). The shape of non-invasively registered ultrasound time-of-flight pulse waves has more clearly expressed arterial and venous peaks comparing with invasively recorded ICP pulse waves (FIG. 8). This is the evidence of very high resolution of ultrasonic ICP/Volume pulse waves measurement because in this case the amplitude of ICP pulse wave was very small—approximately 1.0 mmHg. The preliminary animal study confirm that the non-invasive ultrasonic technology gives accurate information about ICP and ICV dynamics represented by the ultrasound velocity and attenuation in the cerebral parenchyma.

Human study. More than 10 healthy volunteers and 6 ICU coma patients were studied. Body tilting, Queckenstedt, Valsalva and other neurological tests including $CO_2$ reactivity, acetazolamid (Diamox) and nitroglycerin were performed for healthy volunteers studies. Simultaneous invasive (Camino Labs., USA) and our non-invasive ICP monitoring together with ABP and other physiological parameters monitoring of ICU coma patients was carried out.

Our new non-invasive ultrasonic brain injury monitoring technology is based on the following hypothesis: the acoustic properties of the brain parenchymal acoustic path are related with the blood, CSF and parenchyma tissue volume inside this path, these acoustic properties could be measured or monitored non-invasively and in real-time, measured values of ultrasound attenuation and speed (or the time-of-flight) in parenchymal acoustic path can be transformed into intracranial blood volume (IBV) or intracranial pressure (ICP) relative or absolute values.

In the case of healthy volunteers studies it was shown that the physiological changes of ICP and ICP waves as a result of cerebrospinal reactions to the different challenges could be non-invasively measured with high resolution and accuracy.

It was shown that the uncertainty of non-invasive ICP monitor could be less than +/−3.0 mmHg in the case of clinical studies of ICU coma patients applying simultaneous invasive and non-invasive measurements of ICP and including the body tilting tests for the calibration of non-invasive monitor.

Using our non-invasive ICP monitor simultaneously with invasive ICP monitor (Camino), we have investigated the hemodynamic responses of cerebral parenchyma to $CO_2$ reactivity tests and mannitol injections.

For 16 different pathophysiological states of 6 head injured patients we studied ABP, invasive (Camino) and non-invasive ICP monitors were used simultaneously during $CO_2$ reactivity tests and mannitol injections (FIGS. 9, 10, 11, Table 2).

TABLE 2

Correlation between invasive and non-invasive ICP data measured during $CO_2$ reactivity tests in different states of 6 ICU coma patients

| File Name | Correlation Factor | $ICP_0$ Mm Hg | $\Delta_{ICP}$ mm Hg | $ICP_{max}$ Mm Hg |
|---|---|---|---|---|
| S129 | 0.9593 | 2.0 | 16.0 | 18.0 |
| S130 | 0.9808 | 14.5 | 18.5 | 33.0 |
| S131 | 0.9332 | 11.0 | 17.5 | 28.5 |
| S132 | 0.9913 | 12.5 | 16.5 | 29.0 |
| S134 | 0.9651 | 9.0 | 13.5 | 22.5 |
| S135 | 0.9704 | 10.0 | 13.0 | 23.0 |
| S138 | 0.9960 | 12.5 | 23.5 | 36.0 |
| S139 | 0.9824 | 8.0 | 11.0 | 19.0 |

TABLE 2-continued

Correlation between invasive and non-invasive ICP data measured during $CO_2$ reactivity tests in different states of 6 ICU coma patients

| File Name | Correlation Factor | $ICP_0$ Mm Hg | $\Delta_{ICP}$ mm Hg | $ICP_{max}$ Mm Hg |
|---|---|---|---|---|
| S140 | 0.9911 | 8.5 | 19.0 | 27.5 |
| S141 | 0.9836 | 8.0 | 19.5 | 27.5 |
| S143 | 0.9859 | 10.0 | 15.5 | 25.5 |
| S144 | 0.9664 | 10.0 | 12.0 | 22.0 |
| S145 | 0.9722 | 9.0 | 11.0 | 20.0 |
| S149 | 0.9717 | 3.5 | 10.5 | 14.0 |
| S150 | 0.9417 | 4.0 | 8.5 | 12.5 |
| S151 | 0.9725 | 3.5 | 8.0 | 11.5 |

Blood gas analysis was also applied. A parenchymal acoustic path was used for non-invasive measurements and the time dependencies of ultrasound velocity and attenuation were measured. The measured data were compared with simultaneously recorded ICP data. The correlation between invasively and non-invasively measured ICP data was from 0.9332 up to 0.9960 (Table 2) in the range of ICP changes from 2.0 mmHg up to 36.0 mmHg (Table 2). The absolute differences between invasively and non-invasively measured ICP data were within the limits +/−2.0 mmHg (FIGS. 10, 11).

To illustrate the relationship of measured time-of-flight or ultrasound velocity relative changes with the intracranial blood volume (and ICP) pulse waves the non-invasive measurements were performed on the head of cardiological patient (FIG. 12). The upper graph of FIG. 12 is the non-invasively measured ultrasound velocity relative pulsation, the lower graph—simultaneously recorded ECG. It is clearly seen from FIG. 12 that measured ultrasound velocity pulse waves represent the additional intracranial blood volume as a result of cardiac pulsation. The amplitude of non-invasively recorded pulses inside the parenchymal acoustic path is positive. This can be explained by the relationship between relative value of the transintracranial time-of-flight $\Delta TTF/TTF_D$, relative displacement of the skull $\Delta L_l/L_D$ and relative change of ultrasound velocity $\Delta v/v_D$ inside the parenchymal acoustic path:

$$(\Delta TTF/TTF_D) = (\Delta L_l/L_D) - (\Delta v/v_D) \quad (15)$$

From (15) follows that positive $\Delta v/v_D$ pulse waves and negative $\Delta TTF/TTF_D$ pulse waves is the result of $(\Delta L_l/L_D) << (\Delta v/v_D)$. In our animal and human studies we recorded only negative $\Delta TTF/TTF_D$ pulse, waves.

The typical record of transintracranial time-of-flight pulse waves and slow time-of-flight waves (Lundberg's B waves) is shown in FIG. 13. Here $\tau_s$ and $\tau_D$ are transintracranial systolic and diastolic time-of-flight values (FIG. 13A). The envelope of more than 300 pulse waves is shown in FIG. 13B. The slow waves of mean time-of-flight are shown in FIG. 13C. These slow waves represent the slow blood volume changes inside the parenchymal acoustic path caused by the intracranial compliance and ICP mean value dynamics in the ICU coma patient. It is clearly seen from FIG. 13 that the transintracranial time-of-flight pulse waves are negative. It is also seen from FIG. 13 that the envelope of pulse waves is highly correlated with the mean TTF (or intraparenchymal blood volume, or mean ICP) dynamics. This typical result is the additional evidence that the relative skull displacement caused by ICP changes is much less than relative changes of ultrasound velocity inside the parenchymal acoustic path.

It is seen from FIG. 13 that it is possible to identify the artefacts caused by the patients head or body movement comparing the non-invasively measured pulse waves envelope with the slow waves. If the slow waves and pulse waves envelope correlate highly that means that the same physiological or pathophysiological phenomena is the cause of this similarity. If the artefacts occur they disturb that similarity and are automatically identified in the personal computer and eliminated.

To evaluate the influence of the skull displacement $\Delta L_I/L_D$ to the result of $\Delta TTF/TTF_D$ measurement we performed the experiment with the external pressure applied to the hybrid ultrasonic transducers FIG. 1A. The rigid mechanical frame of our apparatus is fixing the distance $L_0$=const (FIG. 1B) with the high accuracy (the possible change of $L_0$ was less than 0.3 micrometers when 200 mmHg external pressure was applied to the mechanical frame to check the rigidity of the frame). The distance $L_0$ cannot be changed by the pulsatile skull displacement in the case when the hybrid transducers are pressed to the human head. In the case when the hybrid ultrasonic transducers are just touching the surface of the head skin, the pulsatile skull displacement is not limited by the external mechanical boundaries. We expected that in the case of pressured ultrasonic transducers and decreased skull pulsatile displacement the member $\Delta L_I/L_D$ of the equation (15) will be decreased and the member $\Delta TTF/TTF_D$ will be increased because the member $\Delta v/v_D$ depends on intracranial blood volume dunamics and does not depend on the external pressure applied to the skull. The experimental results are shown on FIG. 14 and FIG. 15. It is seen from FIG. 14 that, as expected, the external pressure (200 mmHg) to the skull in the places of acoustic contacts between the hybrid ultrasonic transducers and the external tissues reduced the skull pulsation. But the averaged (during 1 hour of pulse waves monitoring) influence of $\Delta L_I/L_D$ is only 10%–11% comparing with 89%–90% influence of $\Delta v/v_D$ to the result $\Delta TTF/TTF_D$ of equation (15). The 10% error caused by free skull pulsation is acceptable during ICP pulse waves and slow waves non-invasive monitoring. This error can be reduced applying physiologically acceptable pressing of the hybrid ultrasonic transducers to the external tissues and skull.

The experimental results obtained by invented apparatus and method confirm the claims.

With further regards to the method and apparatus:
1. Apparatus:
   the PVDF layers are included into the structure of hybrid ultrasonic transducers,
   IP/D converter, TT/D converter, ADC, DSP, time division multiplexer, timing generator are new blocks,
   new connections of new blocks.
2. Method:
   the algorithm is new,
   the possibility to monitor non-invasively and simultaneously intraparenchymal blood volume and parenchyma tissue volume inside the parenchymal acoustic path is new. Having simultaneous diagnostic data of two volumes and having possibility to eliminate external tissue and skull acoustic phenomena it is possible to determine ICP absolute value and monitor this value with the accuracy very close to the accuracy of invasive ICP monitors,
   a lot of procedures are new—receiving of echo signals from internal surfaces of dura matter of the both sides of the human head; analog to digital convertion and digital processing of all copies of ultrasonic signals, received by PVDF and ceramic transducers; time windows generating and adjustment; procedures of TEC+TS and TTF simultaneous measurements; procedures of internal periods measurements, procedures of instrumental delay time measurements; all procedures of elimination of ultrasonic properties of external tissues and skull; very important is a new possibility to identify the artifacts caused by mechanical movement of the patient body or the head comparing the pulse waves envelope dynamics with the ICP man value or slow waves dynamic.

BRIEF DESCRIPTION OF THE DRAWINGS

Enclosed are the graphs (FIGS. 16, 17, 18) which are evidence of the possibility to monitor the intracranial pressure very accurately (error less than 10%) and noninvasively without limitations of the monitoring time. The error 10% in ICP range of 20–100 mmHg is acceptable following the American National Standard for Intracranial Pressure Monitoring Devices. This standard has been developed by the Association for the Advancement of Medical Instrumentation (AAMI) in association with the U.S. Neurosurgery Committee.

FIG. 16A—the monitoring data of ultrasonic pulses instrumental delay time of our apparatus. The delay time is changing within the limits of a few nanoseconds only.

FIGS. 16B and 16C—transcranial delay time on left and right sides of the human head. The meaning of this time is the delay time of ultrasonic signals which were transmitted through the external tissues, skull and dura matter and were reflected by the Intracranial surface of dura matter. These pulses pass external tissues, skull an dura matter twice because of reflection. The delay time presented at FIGS. 16B and 16C is equal to the half of measured time between the moments of transmission and receiving of reflected pulses.

Figure 17:
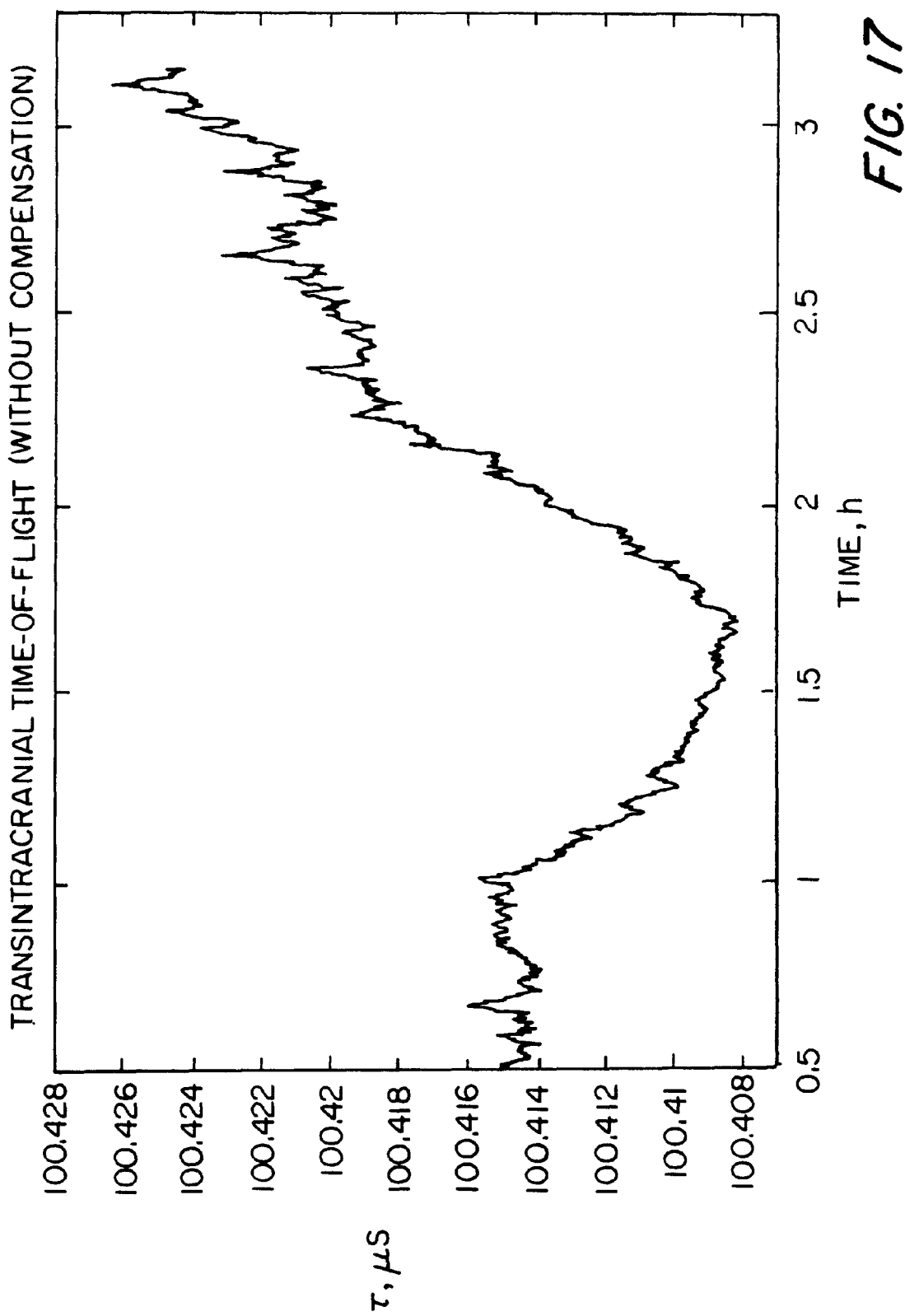

FIG. 17—the transintracranial time-of-flight through the left layers of external tissues, skull, dura matter, intracranial media and right layers of dura matter, skull and external tissues. The data presented in FIG. 17 is obtained using transmission of ultrasonic pulses from the left side of the human head to the right side and after than, from the right side to the left side. The data presented in FIG. 17 is the average of two such periodical cycles.

Figure 18:
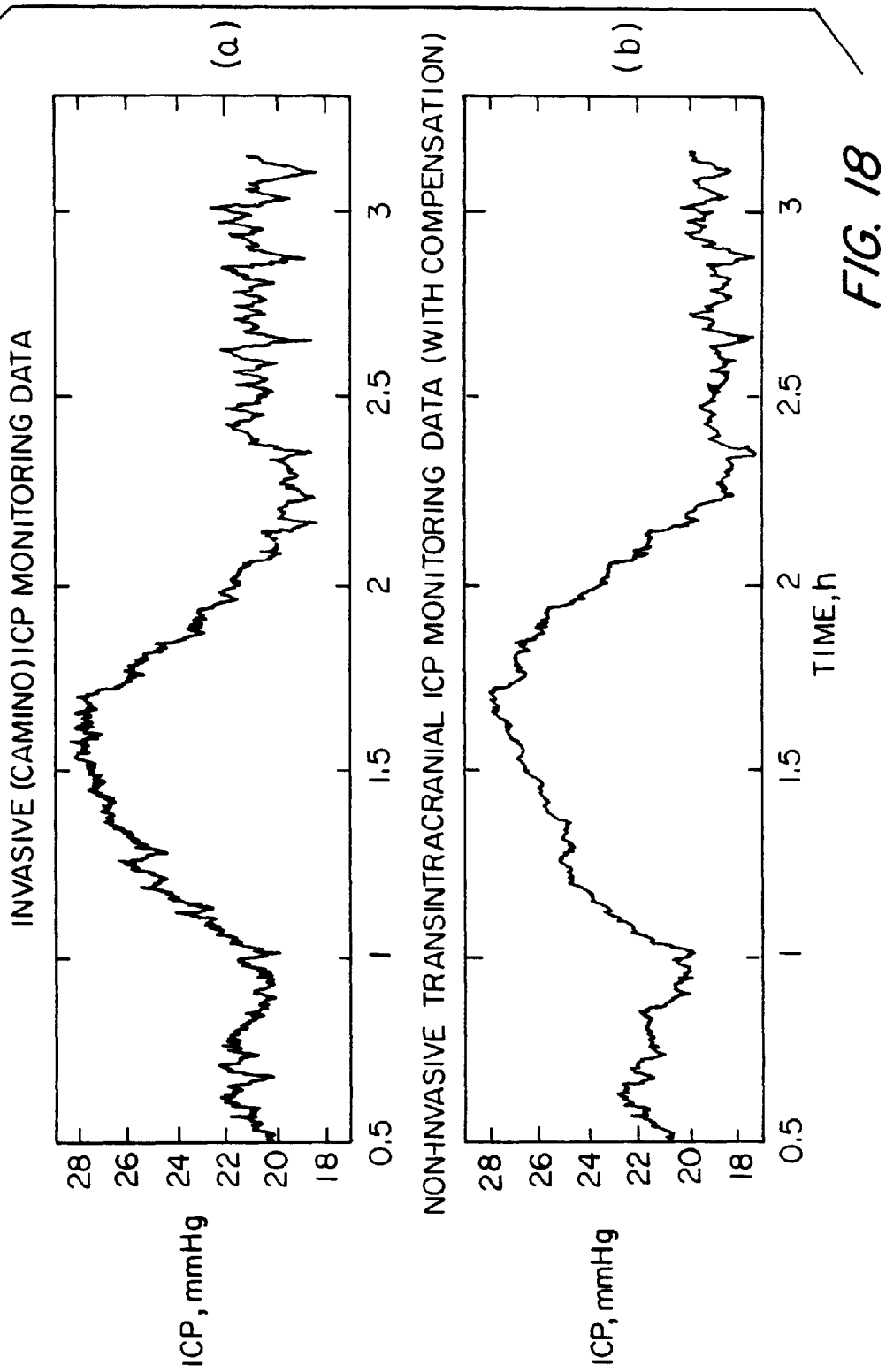

FIG. 18 is the comparison of simultaneously-recorded invasive and noninvasive ICP data during long term continuous monitoring. Noninvasive transintracranial ICP monitoring data were calculated by the following steps:

To get the transintracranial time-of-flight data with compensation the instrumental delay data (FIG. 16A) were added to the data of the left and right transcranial delay time (FIGS. 16B and 16C). The result was subtracted from the transintracranial time-of-flight data (FIG. 17). The result of such compensation is the time-of-flight of ultrasonic pulses from one Intracranial surface to the other Intracranial surface of Intracranial dura matter. This result depends on the intracranial hemodynamic phenomena of the parenchymal acoustic path only and does not depend on the hemodynamic phenomena in the external tissues, delay time inside the skull or dura matter and instrumental delay time. The possible spontaneous movements of the mechanical frame caused by the movement of the patient body are also compensated in this case. The calculated value of the compensated transintracranial time-of-flight is transformed into absolute values of ICP, mmHg (FIG. 18) applying the linear transform of the reciprocal values of compensated transintracranial time-of-flight. These reciprocal values are proportional to the ultrasound velocity inside the parenchymal acoustic path.

Figure 16:
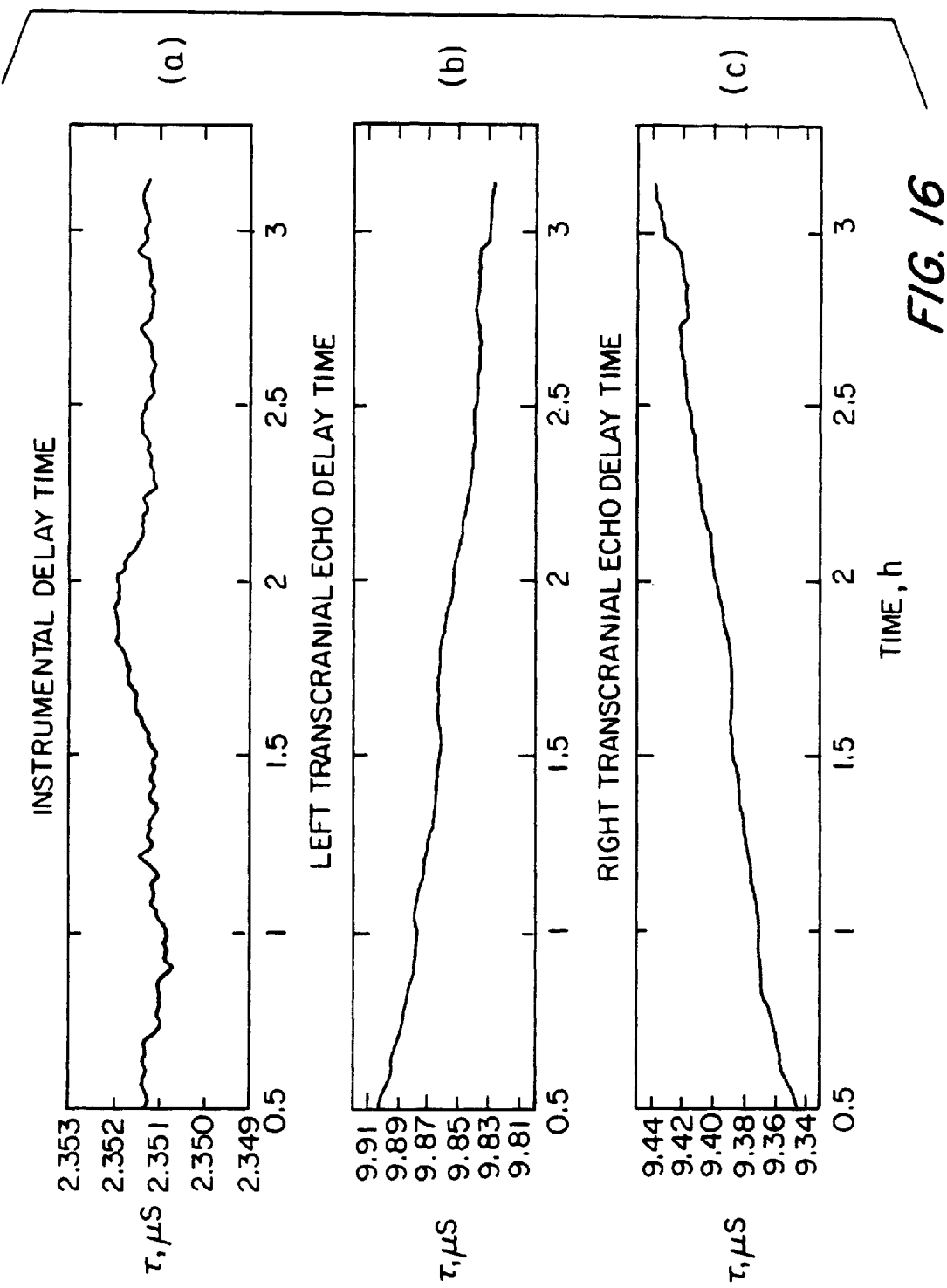

All the calculations are performed in real time. The only graph FIG. 18B is displayed. FIG. 16 and FIG. 17 represent the internal instrumental data which are used to get the FIG. 18B in real time The data in FIG. 18 show that the proposed method of the automatic real time in situ and in status nascendi compensation of external tissue phenomena, the instrumental delay time and the delay time in the skull and dura matter layers is the only way to monitor continuously and noninvasively the absolute ICP values.

What is claimed is:

1. An ultrasonic investigating method for determining an indication of a characteristic of the intraparenchymal tissue comprising the steps of:

transmitting a broad band ultrasonic pulse from an ultrasonic transducer located on one side of the cranium of a person to an ultrasonic detector located on another side of the cranium for generating a received signal on the output of the detector;

decomposing the received signal into narrowband components;

determining parameters from said components including group delay, phase angle and attenuation of the components through their travel within said cranium; and deriving from said parameters a characteristic of said intraparenchymal tissue within said cranium.

2. The method of claim 1 and further including the steps of:

determining the overall travel times of the components through said cranium;

determining the travel times of the components through intermediate matter located adjacent sides of and within the cranium;

removing the travel times of the components through said intermediate matter from the overall travel times to derive an indication of the travel time of the components through said intraparenchymal tissue.

* * * * *